US010052291B2

(12) United States Patent
Hansen et al.

(10) Patent No.: US 10,052,291 B2
(45) Date of Patent: Aug. 21, 2018

(54) COMPOSITIONS COMPRISING ELECTROHYDRODYNAMICALLY OBTAINED FIBRES FOR ADMINISTRATION OF SPECIFIC DOSES OF AN ACTIVE SUBSTANCE TO SKIN OR MUCOSA

(71) Applicant: DERMTREAT APS, Virum (DK)

(72) Inventors: Jens Hansen, Virum (DK); Lars Hellerung Christiansen, Klampenborg (DK)

(73) Assignee: DERMTREAT APS, Virum (DK)

( * ) Notice: Subject to any disclaimer, the term of this patent is extended or adjusted under 35 U.S.C. 154(b) by 0 days.

(21) Appl. No.: 15/317,306

(22) PCT Filed: Jun. 9, 2015

(86) PCT No.: PCT/EP2015/062842
§ 371 (c)(1),
(2) Date: Dec. 8, 2016

(87) PCT Pub. No.: WO2015/189212
PCT Pub. Date: Dec. 17, 2015

(65) Prior Publication Data
US 2017/0119690 A1 May 4, 2017

(30) Foreign Application Priority Data

Jun. 10, 2014 (DK) .................................. 2014 70342
Dec. 22, 2014 (DK) .................................. 2014 70815

(51) Int. Cl.
| | |
|---|---|
| A61K 9/70 | (2006.01) |
| D01D 1/02 | (2006.01) |
| D01D 5/00 | (2006.01) |
| A61K 31/573 | (2006.01) |
| A61K 31/4745 | (2006.01) |
| A61K 47/32 | (2006.01) |
| A61K 47/36 | (2006.01) |
| A61K 47/10 | (2017.01) |
| A61K 9/00 | (2006.01) |
| D01F 6/52 | (2006.01) |
| D01F 6/56 | (2006.01) |

(52) U.S. Cl.
CPC ............ *A61K 9/70* (2013.01); *A61K 9/006* (2013.01); *A61K 9/0014* (2013.01); *A61K 9/0092* (2013.01); *A61K 31/4745* (2013.01); *A61K 31/573* (2013.01); *A61K 47/10* (2013.01); *A61K 47/32* (2013.01); *A61K 47/36* (2013.01); *D01D 1/02* (2013.01); *D01D 5/003* (2013.01); *D01F 6/52* (2013.01); *D01F 6/56* (2013.01); *D10B 2201/30* (2013.01); *D10B 2321/08* (2013.01); *D10B 2321/12* (2013.01); *D10B 2331/06* (2013.01); *D10B 2509/00* (2013.01)

(58) Field of Classification Search
None
See application file for complete search history.

(56) References Cited

U.S. PATENT DOCUMENTS

| | | | |
|---|---|---|---|
| 7,390,760 B1 * | 6/2008 | Chen ..................... | A61F 13/514 442/340 |
| 2003/0017208 A1 * | 1/2003 | Ignatious ................ | A61K 9/70 424/486 |
| 2003/0069369 A1 * | 4/2003 | Belenkaya ........ | A61F 13/00042 525/437 |
| 2009/0269392 A1 | 10/2009 | Tauber et al. | |
| 2010/0190254 A1 * | 7/2010 | Chian ................. | A61L 27/3847 435/396 |
| 2010/0254961 A1 | 10/2010 | Nishio et al. | |
| 2010/0323573 A1 * | 12/2010 | Chu ....................... | B01D 65/08 442/153 |
| 2011/0111012 A1 * | 5/2011 | Pepper .............. | A61F 13/00995 424/445 |
| 2014/0128345 A1 | 5/2014 | Woodrow et al. | |

FOREIGN PATENT DOCUMENTS

WO  WO 2006/106514 A2  10/2006
WO  WO 2010/099292 A2  9/2010

OTHER PUBLICATIONS

Ignatova et al., European Polymer Journal, 43, pp. 1609-1623. (Year: 2007).*
Son et. al., Polymer, 45, pp. 2959-2966 (Year: 2004).*
Unnithan et al., "Wound-dressing materials with antibacterial activity from electrospun polyurethane-dextran nanofiber mats containing ciprofloxacin HCl," Carbohydrate Polymers, vol. 90, No. 4, pp. 1786-1793, Nov. 2012.
Tonglairoum et al., "Fast-Acting Clotrimazole Composited PVP/HP[beta] CD Nanofibers for Oral Candidiasis Application," Pharmaceutical Research, vol. 31, No. 8, pp. 1893-1906, Feb. 2014.
Wongsasulak et al., "Effect of entrapped [alpha]-tocopherol on mucoadhesivity and evaluation of the release, degradation, and swelling characteristics of zein-chitosan composite electrospun fibers," Journal of Food Engineering, vol. 120, pp. 110-117, Jan. 2014.
Xiaoqiang et al., "Electrospun polyvinyl-alcohol nanfibers as oral fast-dissolving delivery system of caffeine and riboflavin," Colloids and Surfaces, vol. 103, pp. 182-188, Oct. 2012.
Tyagi et al., "Electrospun Nanofiber Matrix with a Mucoadhesive Backing Film for Oramucosal Drug Delivery," International Journal of Materials, Mechanics and Manufacturing, vol. n+, pp. 81-85, Jan. 2014.
International Search Report dated Jul. 23, 2015 in application No. PCT/EP2015/062842.

* cited by examiner

*Primary Examiner* — Abigail Vanhorn
(74) *Attorney, Agent, or Firm* — Foley & Lardner LLP

(57) ABSTRACT

The present invention relates to electrospun fibers comprising i) a hydrophilic polymer that is soluble in a first solvent, ii) a bioadhesive substance that is slightly soluble in said first solvent, iii) optionally, a drug substance.

30 Claims, 16 Drawing Sheets

Fabrication of drug-delivery layer
Optimisation of electrospinning method

Manufacturing method

Based on protocol:

- 10 wt% PVP (Kollidon 90F, BASF) in ethanol
- Solution volume = 2 mL
- Distance = 17 cm
- Voltage = 14 kV
- Flow rate = 10 ml h$^{-1}$
- 20 gauge needle
- Ambient temperature and

Fabrication of drug-delivery layer

Fabrication of dyed materials

- Alcian blue 8GX (Merck)
  - ✓ To observe gel in bioadhesion studies
  - ✓ Powdered
  - ✓ Dissolves in ethanol

- Demonstrates potential of electrospun materials to encapsulate and deliver dissolved substances
  - ✓ Ethanol-soluble drugs 10 wt% PVP + 1 w/v % alcian blue in ethanol solution Optical microscopy

Fabrication of drug-delivery layer

Solubility of electrospun materials

- Fast dissolution of PVP in water
  - ✓ < 1 second
- Gel with bioadhesive properties
- Rapid drug release Bioadhesiveness test of PVP/PCL on pig mucosa Solubility test on artifical saliva Eudragit L100-55 + Sodium alginate

A                                      B

Eudragit L100-55 + Sodium carboxymethyl cellulose

C                                      D

Eudragit L100-55 + Chitosan

A  B

Eudragit L100-55 + Poly(vinyl alcohol)

C  D

1) L100-55
2) L100-55 + Dextran
3) L100-55 + Polyethylene oxide
4) L100-55 + Carboxymethyl cellulose
5) L100-55 + Poly(vinyl alcohol)
6) L100-55 + Chitosan
7) L100-55 + Alginate

COMPOSITIONS COMPRISING ELECTROHYDRODYNAMICALLY OBTAINED FIBRES FOR ADMINISTRATION OF SPECIFIC DOSES OF AN ACTIVE SUBSTANCE TO SKIN OR MUCOSA

FIELD OF THE INVENTION

The invention relates to drug-containing electrohydrodynamically obtained fibres and to compositions comprising said fibres for application on the skin, the lips or mucosa to deliver a specific amount of the one or more drug substances to the skin or mucosa. The formulation principle ensures the presence of the bioadhesive substance in the fibres in the form of undissolved material, which enables in situ bioadhesion upon contact with eg saliva in the oral cavity. The fibres are in the form of a layer and may be provided with one or more further layers, eg a backing layer that is insoluble in water or saliva and/or a layer that may influence the release of the drug substance from the final composition.

Moreover, the compositions are suitable for local application to internal wet surfaces such as vocal cord or the bowel eg for treatment of inflammatory bowel disease. Notably, the invention relates to compositions comprising electrohydrodynamically obtained fibres for application to the oral cavity to deliver a drug substance to the oral mucosa.

BACKGROUND OF THE INVENTION

One or the major problems relating to treatment of diseased in the skin or mucosa is to deliver a correct amount of the drug substance to the diseased skin or mucosa. Compositions for use in the treatment of diseases in the skin or mucosa are very often in the form of a creme, an ointment or a gel, which is applied by the patient by spreading a variable amount of the composition on a diseased area of variable size, and the composition is spread on the area in a layer of variable thickness.

Accordingly, it is normally very difficult to obtain reliable results regarding eg relation-ship between dose and effect, inter- and intraindividual variations etc.

Transdermal systems like plasters are normally used for drug substances that must penetrate the skin, i.e. they are not intended for use in the treatment of diseases of the skin or mucosa, where the drug substances should act locally on or within the skin or mucosa. U.S. Pat. No. 4,765,983 relates to an adhesive medical tape for use in stomatitis. The tape comprises a support layer consisting of an intestine soluble polymer and at least two medicament-containing layers consisting essentially of a water-soluble polymer containing a steroid.

The variability of dosage makes it very difficult to control treatment of a skin or mucosa disease and to make a correct decision regarding continuing or discontinuing treatment as it eg may be difficult to judge the benefit/risk profile for the treatment. If eg systemic side effects are observed then it is difficult to know whether the side-effects are due to over-dosing (the patient applies a too large dose by eg spreading the composition over a too large area, or the patient spreads the composition in a too thick layer) or whether the side-effects can only be avoided by termination of the treatment. Under-dosing may also be a problem in the topical therapy, especially when creams, ointments, lotions or other liquid or semi-liquid compositions are used. In general, 30% of patient undergoing topical treatment is subject to under-dosing.

In order to have a pharmaceutical composition approved by the regulatory health authorities, substantial documentation relating to the therapeutic effect, indication, side effects, toxic effects, dosages etc. is required. To this end it would be advantageous if effects relating to variability in dosages could be avoided or substantial reduced, i.e. if it is possible to ensure that the dose applied is controlled and not subject to the judgement of the patient applying the composition (eg area, thickness, frequency etc.). In this manner a more reliable benefit/risk profile could be obtained.

Moreover, in order to be effective the compositions for use in the treatment of diseases in the oral mucosa must stay on the diseased site for a specific period of time. Often compositions like eg films are not intended to be used in the treatment of diseased in the oral cavity, but are used to obtain a relatively fast absorption into the systemic circulation. Films normally disintegrate relatively fast, which either makes them unsuitable for use or they may be applied many times daily.

Another problem relates to administration to the oral cavity or other mucosa located in a humid environment such as vagina, ocular mucosa etc. Many diseases are located to the oral cavity and require local treatment (eg oral lichen planus). Such treatment is often by use of solutions, cremes, pastes, or ointments, where it is administered by spreading the composition on the diseased area with a finger. In addition to the disadvantages mentioned above, saliva produced by the salivary glands together with movements of the tongue tends to remove the composition from the administration site and will reduce the effect of the treatment.

Thus, there is a need for developing compositions for treatment of a disease located to the skin or mucosa or as described in the Field of the invention, wherein the compositions are designed in such a manner that a specific dose easily can be applied to the diseased area. Notably, the composition may stay on the application site for a prolonged period of time.

DESCRIPTION OF THE INVENTION

Figure 1:
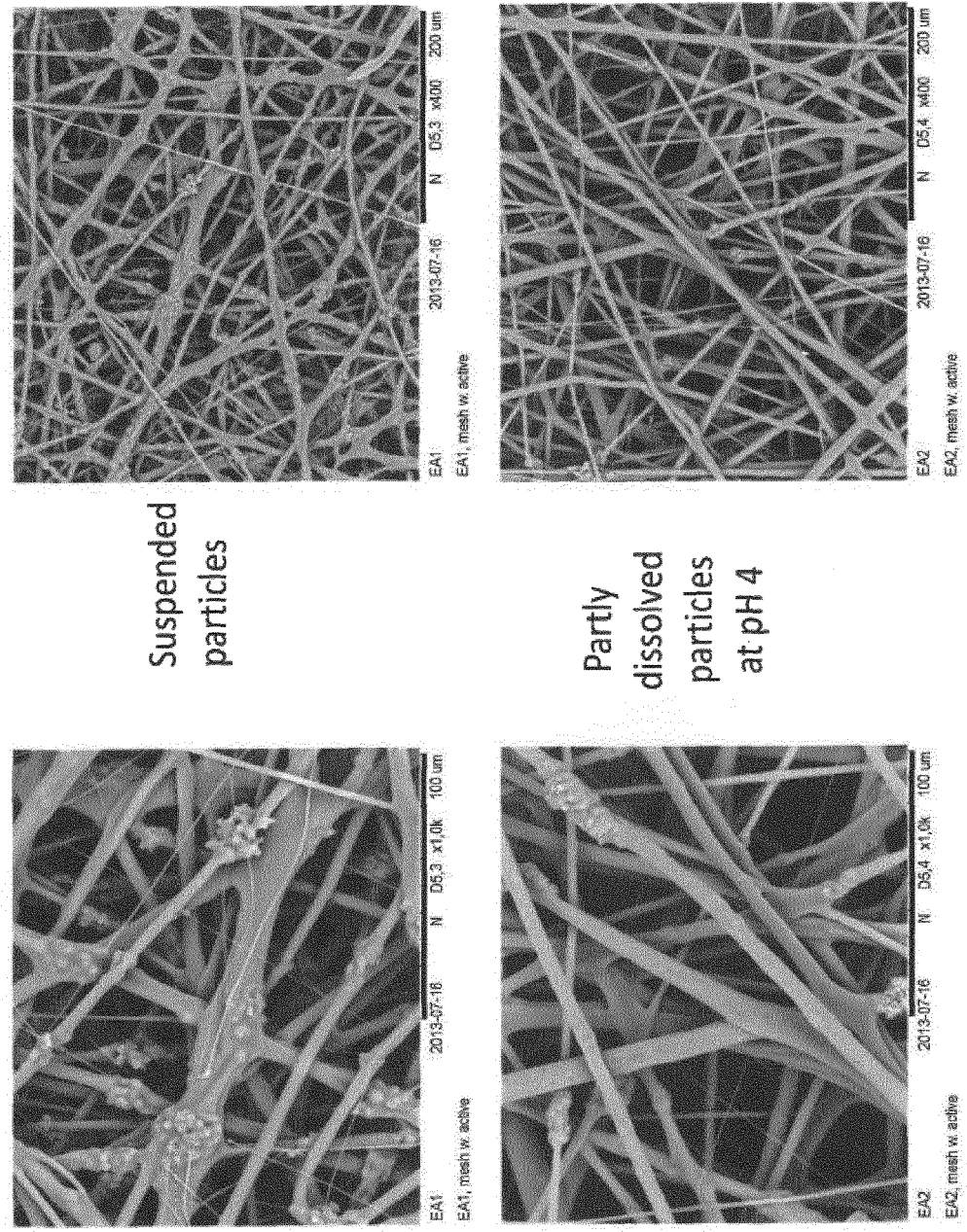
FIG. 1 shows electron microscopic pictures of electrospun fibres according to the invention.

The present invention provides electrohydrodynamically obtained fibres comprising
i) a fibre-forming hydrophilic polymer that is soluble in a first solvent,
ii) a bioadhesive substance that is slightly soluble in said first solvent,
iii) a drug substance.

In a separate aspect the invention relates to electrohydrodynamically obtained fibres comprising
i) a fibre-forming hydrophilic polymer that is soluble in a first solvent,
ii) a bioadhesive substance that is slightly soluble in said first solvent,
i.e. fibres that are analogous to the fibres mentioned above, but without any content of a drug substance. All the details mentioned herein regarding the fibre-forming hydrophilic polymer, the bioadhesive substance, concentrations thereof, ratios between the bioadhesive substance and the fibre-forming hydrophilic polymer and compositions comprising such fibres apply mutatis mutandis to the fibres or compositions without any content of a drug substance. The present inventors have found that such fibres or compositions comprising such fibres may be suitable for use in specific cases such as to treatment of uncomplicated wounds eg in the oral cavity.

In the present context, the term electrohydrodynamically obtained fibres is intended to denote that the fibres are obtained by a method that involves electrostatic The overall term for such methods is electrohydrodynamic (EHD) methods and includes electrospinning, electrospraying, coaxial electrospinning, coaxial electrospraying, emulsion electrospinning, etc. Such methods are intended to be part of the present invention in relation to preparation of the fibres according to the invention. For practical reason the term "electrospun fibres" are used, but is intended not to be limited to fibres obtained by electrospinning, but to fibres obtained by an electrohydrodynamic method as described above.

The electrospun fibres are provided in a thin layer, which adheres to the skin, mucosa or a humid internal surface. The drug substance is homogeneously distributed in the electrospun fibres, whereby the concentration of drug substance per surface area of the layer is constant and a dose of the drug substance can easily be determined by using a measured area of the layer.

An important feature of the present invention is to use a combination of a fibre-forming hydrophilic polymer and a bioadhesive substance, where the two substances have different solubilities in specific solvents. Thus, the fibre-forming hydrophilic substance must be soluble in a solvent, whereas the bioadhesive substance should not dissolve or at least only a small amount of the bioadhesive substance should dissolve.

The solvent may be C1-C3 alkanol such as methanol, ethanol, propanol or isopropanol, or mixtures thereof. The solvent or solvent mixture may also contain at the most 20% v/v of an aqueous medium such as water.

In some cases, the solvent is ethanol or ethanol-water mixtures. Ethanol may contain up to 20% v/v water, normally about 3-10% v/v.

The solvent or solvent mixture (in the following commonly denoted "solvent") used in the preparation of the fibres. Thus, to prepare the fibres the ingredients are contained in the solvent; the hydrophilic polymer is dissolved in the solvent and the bioadhesive substance is in undissolved form or at least 90% w/w of the bioadhesive substance is in undissolved form. The ingredients are dissolved/dispersed in the same type of solvent, but may be applied in the electrospinning process as one, two or three different mixtures.

The solubilities of the hydrophilic polymer and the bioadhesive substance in the solvent used are important in order to obtain the desired properties of the fibres of the invention. Thus, the hydrophilic polymer must have a solubility in a first solvent of 3 g/100 ml or more at 25° C. or 10 g/100 ml or more at 25° C., and the bioadhesive substance must have a solubility in said first solvent of 0.5 g/100 ml or less at 25° C. or 0.1 g/100 ml or less at 25° C.

Due to the difference in solubility the bioadhesive substance is attached to the fibres as small particles. A small amount of the bioadhesive substance may be dissolved in the solvent and may therefore be an integral part of the fibres, but in order to achieve maximal bioadhesive effect it is contemplated that the bioadhesive substance is attached to the fibres and that the fibrous structure essentially is due to electrospinning of the fibre-forming hydrophilic polymer.

Dependent on the properties of the drug substance it may be an integral part of the fibres or may be attached to or admixed with the fibres. Thus, if the drug substance is soluble in the solvent used and capable of forming fibres, then it may be an integral part of the fibres. If these conditions not are present the drug substance will be attached to the fibres of present in admixture with the fibres.

In the present context the term "integral part of the fibres" means that the substance together with the fibre-forming hydrophilic polymer form the fibrous structure of the fibres.

The hydrophilic polymer is the basic ingredient in the electrospun fibres and is the ingredient that has the ability to form a fibre material. In order to avoid any confusion with other ingredients present either in the electrospun fibres or in a composition thereof the term "fibre-forming hydrophilic polymer" is used in the following. The fibre-forming hydrophilic polymer is suitably a polymer that is soluble in or forms a gel in a $C_1$-$C_3$ alkanol such as methanol, ethanol, propanol or isopropanol, notably ethanol, propanol or isopropanol. The spinning process requires that the polymer, which is the main component of the fibres, is in dissolved form to allow a steady stream of the dissolved polymer to flow from a needle to a grounded collecting plate in a jet-like fashion during the spinning process.

Suitable fibre-forming hydrophilic polymers are polyvinylpyrrolidone (PVP), acrylates and acrylic copolymers (eg Eudragit®), and mixtures thereof. Other polymers like eg ethylcellulose (EC), hydroxypropylcellulose (HPC), or mixtures thereof may also be used. Ethylcellulose (EC), hydroxypropylcellulose (HPC), or mixtures thereof may especially be used in combination with polyvinylpyrrolidone (PVP) and/or acrylates including acrylic copolymers (eg Eudragit®) In the examples especially PVP and acrylic copolymers have been used.

Polyvinylpyrrolidone can be used in a grade having an approximate molecular weight of from 2,500 Da to 3,000,000 Da (eg Povidone with K-values of from 12 to 120). PVP can be purchased as Kollidon®:

| Kollidon ® | Weight average molecular weight $M_w$ |
|---|---|
| 12PF | 2,000-3,000 |
| 17PF | 7,000-11,000 |
| 25 | 28,000-34,000 |
| 30 | 44,000-54,000 |
| 90F | 1,000,000-1,500,000 |

In the low MW-range suitable grades are contemplated to have a MW of from about 25,000 to about 120,000 Da, notably from about 70,000 to about 100,000 Da. In the examples herein Kollidon® 90F has mainly been used and accordingly, a preferred PVP has a $M_w$ of from about 900,000-about 3,000,000, notably from about 1,000 to about 1,500,000.

Ethylcellulose is sold under the trademark ETHOCEL™ (Dow Chemical Company) and is available in many different grades. Dow Chemical Company produces ethylcellulose in two ethoxyl types (denoted Standard and Medium). Dependent on its ethoxyl content ethylcellulose may have different softening point and melting point temperatures. Ethylcellulose is also produced in a number of different viscosities. In the table below is given a listing of available ethylcelluloses.

| ETHOCEL polymers | | |
|---|---|---|
| Product viscosity designation | Viscosity range mPa * s | Ethoxyl content % Standard 48.0-49.5 | Ethoxyl content % Medium 45.0-46.5 |
| 4 | 3-5.5 | ETHOCEL Std. 4 | |
| 7 | 6-8 | ETHOCEL Std. 7 | |
| 10 | 9-11 | ETHOCEL Std. 10 | |
| 14 | 12.6-15.4 | ETHOCEL Std. 14 | |

ETHOCEL polymers

| Product viscosity designation | Viscosity range mPa * s | Ethoxyl content % Standard 48.0-49.5 | Ethoxyl content % Medium 45.0-46.5 |
|---|---|---|---|
| 20 | 18.22 | ETHOCEL Std. 20 | |
| 45 | 41.49 | ETHOCEL Std. 45 | |
| 50 | 45-55 | | ETHOCEL Med. 50 |
| 70 | 63-77 | | ETHOCEL Med. 70 |
| 100 | 90-110 | ETHOCEL Std. 100 | ETHOCEL Med. 100 |
| 200 | 180-220 | ETHOCEL Std. 200 | |
| 300 | 270-330 | ETHOCEL Std. 300 | |
| 350 | 250-385 | ETHOCEL Std. 4 | |

In plasticized form it has excellent thermoplasticity and is useful for compositions made by molding, extrusion or lamination. Ethylcellulose is also an excellent film-former and is used in coating of eg tablets. The above-mentioned ethylcellulose qualities have an ethoxyl content of at least 45.0% and, accordingly they are soluble in ethanol and practically insoluble in water.

Acrylates and acrylic acid derivative include polymethacrylates, methacrylate copolymers, acrylic copolymers and methacrylate polymers. Preferred acrylates are those sold under the trademark EUDRAGIT®, which are soluble in ethanol, or acrylates/octaacrylamide copolymer (sold under the name DERMACRYL 79). These include EUDRAGIT®E 12,5 (amino methacrylate copolymer), EUDRAGIT® E100 (amino methacrylate copolymer; basic butylated methacrylate copolymer), EUDRAGIT®E PO ((amino methacrylate copolymer), EUDRAGIT®L 100-55, EUDRAGIT®L 100 (methacrylic acid-methyl methacrylate copolymer 1:1), EUDRAGIT®S 100 (methacrylic acid-methyl methacrylate copolymer 1:2), EUDRAGIT®RL 100, EUDRAGIT®RL 100 (ammonio methacrylate copolymer type A), EUDRAGIT®RL PO, EUDRAGIT®RS 100 (ammonio methacrylate copolymer type B), EUDRAGIT®RS PO. EUDRAGIT®E is a cationic polymer based on dimethylaminoethyl methacrylate and other neutral methacrylic acid esters: EUDRAGIT®L and S are methacrylic acid copolymers and are cationic copolymerization products of methacrylic acid and methyl methacrylate. EUDRAGIT®RL or RS is ammonio methacrylate copolymers synthesized from acrylic acid and methacrylic acid.

EUDRAGIT® E 100 is soluble up to pH 5.5 and E 12.5 is soluble above pH 5.

EUDRAGIT® L30 D-55, L-100-55 (methacrylic acid-ethyl acrylate copolymer 1:1), L 100, L 12,5, are normally used in enteric formulations, but may be used in order to delay release of the drug substance from fibres of the invention. EUDRAGIT® L30 D-55, and L-100-55 dissolve at a pH about 5.5 and the grades L 100 and L 12,5 dissolve at pH 6 or above.

As the pH in saliva normally is about 5-6 these polymers are of interest for fibres for oral use. If sustained or prolonged release is desired polymers being soluble at lower of higher pH may be more suitable for use.

EUDRAGIT® products are also available for sustained-release formulations and such grades may be of interest to incorporate in fibres of the invention either alone or together with another hydrophilic polymer. Relevant grades belong to the RL, RS, NE and NM series such as RL 100, RL PO, RL 30D, and RL 12,5, RS 100, RS PO, RS 30D, and RS 12,5, NE 30D and NE 40D, and NM 30D.

Hydroxypropylcellulose is a non-ionic water-soluble cellulose ether. It combines organic solvent solubiltiý, thermoplasticity and surface activity and that thickening and stabilizing properties. The fibres are flexible and non-tacky at high humidity. Hydroxypropylcellulose is sold under the name KLUCEL™.

In the present context, the preferred fibre-forming hydrophilic polymers are selected from PVP, hydroxypropylcellulose (HPC), acrylates and acrylic acid derivatives, and mixtures thereof.

The concentration of the fibre-forming hydrophilic polymer(s) in the fibres according to the invention is normally from about 40% to about 92% w/w notably from about 50 to about 85% w/w or from about 60% to 75% w/w.

Fibres of the invention also contain a bioadhesive substance. In order to ensure an easy manufacture of the fibres and to obtain the desired bioadhesive properties in situ after application to the mucosa, it is important that the bioadhesive in itself does not contribute significantly to the viscosity of a solution containing the fibre-forming hydrophilic polymer.

In the present context the term "bioadhesive" or "bioadhesion" indicates attachment to a specified biological location such as to the surface of the skin, a lip or a mucosal surface. A bioadhesive substance imparts bioadhesiveness to the drug-containing fibres of the invention or, in certain cases it may be included in a composition of the invention eg as a separate layer, which—after application—is the inner layer facing the skin or mucosa, i.e. the layer that is in contact with the skin or mucosa.

The bioadhesive substance for use in the present context can be selected from dextran, polyethylene oxides, alginate, tragacanth, carrageenan, pectin, gelatin, guar, xanthan, gellan, methylcellulose, hydroxypropylmethylcellulose (HPMC), carboxymethylcellulose and alkali salts thereof, polymers of acrylic acids (PAA derivatives), chitosan, lectins, thiolated polymers, polyox WSRA, PAA-co-PEG (PEG is polyethylene glycol), and mixtures thereof.

In general it is expected that the adhesive effect of polymers increases with increasing molecular weight. Thus, in general adhesive polymers having relatively high molecular weight are preferred.

Polyethylene oxide can be used in grade having an approximate molecular weight of from 100,000 to 4,000,000. Preferred grades have an average molecular weight of from about 700,000 to about 4,000,000. Polyethylene oxide is sold under the name POLYOX™ (Dow Chemical Company) with molecular weights ranging from 100,000 to 7,000,000 Da. As seen from the examples herein suitable polyethylene oxides have a molecular weight of 2,000,000 Da or more such as from 2,000,000-7,000,000 Da.

Dextran can be used in grade having an approximate molecular weight of from 400,000 Da to about 2,000,000 Da. Preferred dextrans have a molecular weight of from about 500,000 to about 2,000,000 Da notably from about 700,000 to about 800,000 Da or from about 1,000,000 to about 2,000,000 Da.

Cellulose derivatives include hydroxypropylmethylcellulose, methylcellulose and carboxymethylcellulose.

Methylcellulose is sold under the name METHOCEL™ (Dow Chemical Company) and is available in a wide range of viscosity grades (from less than 3 to over 100,000 mPA*s).

HPMC is sold in various qualities depending on the viscosity. HPMC is sold under the names Metocel® and Klucel®. A suitable HPMC has an average molecular weight from about 80,000 to about 140,000.

Carboxymethylcellulose is available in a broad selection of grades. The viscosity ranges from 10 to 100,000 mPa*s. It is also available as its sodium salt with a broad range of substitution levels. Dow Chemical Company sells sodium carboxymethylcellulose under the name WALOCEL™.

Polyvinylalcohol can be used in grade having an approximately molecular weight of from 20,000 Da to 200,000 Da.

Preferred bioadhesive substances are polyethylene oxides, dextrans or combinations thereof.

The inclusion of a bioadhesive substance in the fibres according to the invention makes is possible to obtain a final formulation that is bioadhesive and can remain on the skin or mucosal surface for a prolonged period of time without falling off.

The amount of the bioadhesive substance in the fibres per surface area is important in order to ensure a suitable bioadhesion.

The concentration of the bioadhesive substance in the fibres is from about 5% to about 60% w/w, notably from about 8% to about 50% or from about 10% to about 40% w/w, based on the sum of the total dry weight.

The present inventors have found that the weight ratio between the bioadhesive substance and the hydrophilic polymer in the fibres should be in a range of from 0.1 to 10 such as from 0.2 to 10. It may depend on the particular hydrophilic polymer and the particular bioadhesive substance used, but the above mentioned range is normally applicable. The ratio will to a certain degree depend on the bioadhesive substance chosen so that the higher bioadhesive potential, the bioadhesive substance has, the lower ratio is required and vice versa. The numbers given are, however, regarded as general guidance. In the examples herein further examples are given. In particular suitable results have been obtained when the weight ratio between the bioadhesive substance and the hydrophilic polymer is from 0.1 to 4 or from 0.1 to 2.

The fibres according to the invention also contain a drug substance. The drug substance is selected from drug substances, which are indicated for treatment of a disease of the skin, lip, or mucosa, or in the case, where the fibres are included in compositions for application on an internal surface as described here, the drug substance may be any drug substance that is indicated for the specific treatment. In the present context, the drug substance may be selected from drug substances, which are indicated for treatment of a disease in the oral cavity such as a drug substance that is indicated for local treatment of a disease in the oral cavity. Drug substances of particular interest are mentioned herein. The drug substance may be present in dissolved, undissolved or partly dissolved form dependent on the drug solubility in the hydrophilic polymer and bioadhesive substance used.

The fibres according to the invention may also contain one or more pharmaceutically acceptable excipients including those mentioned herein. Besides the excipients mentioned herein below, the fibres may contain a plasticizer. The plasticizer imparts a certain plasticity to the fibres, it may facilitate the manufacturing process and/or improve the flexibility and processability of the hydrophilic polymer(s). Examples of suitable plasticizers are citric acid esters like acetyl triethyl citrate, tributyl citrate or triethylcitrate, castor oil, diacetylated monoglycerides, dibutyl sebacate, diethyl phthalate, sorbitol, glycerol or glycerol derivatives like triacetin or tributyrin, a cellulose derivative like cellulose nitrate, glycols like polyethylene glycols notably polyethylene glycols with a molecular weight from about 100 to about 1500, polyethylene glycol monomethyl ether, propylene glycol, or mixtures thereof.

A plasticizer may affect the release rate of the drug substance. Accordingly, a plasticizer may also be regarded as a release rate modifier. Normally, a change in concentration of plasticizer will affect the release rate. Normally and if present the concentration of a plasticizer in the fibres is in a range of from 0 to about 10% w/w such as from about 0.5 to about 5% w/w.

The electrospun fibres may also contain a solubility improving agent in order to adjust or manipulated the release rate of the drug substance from the electrospun fibres. If present, the drug substance is dissolved in the solubility improving agent and, optionally in one or more volatile solvents, notably a $C_1$-$C_3$ alkanol, before fed into the apparatus making the electrospun fibres. In this manner it is ensured that the solubility improving agent containing drug substance is located within the electrospun fibres. Suitable solubility improving agents include a polyoxyethylene fatty alkyl ester, an isopropyl ester of a straight or branched $C_8$-$C_{14}$ fatty acid, a propylene glycol mono- or diester of a $C_8$-$C_{14}$ alkanol or alkenol, a straight or branched $C_8$-$C_{24}$ alkanol or alkenol, a $C_6$-$C_{22}$ acylglyceride, N-alkylpyrrolidone or N-alkylpiperidone, and a mineral oil such a paraffin.

The polyoxyethylene fatty alkyl ester is suitably selected from the group consisting of polyoxyethylene-15-stearyl ether, polyoxyethylene-11-stearyl ether, polyoxyethylene-14-butyl ether, polyoxyethylene-10-cetyl ether, and polyoxyethylene-3-myristyl ether.

The isopropyl ester of a straight or branched $C_8$-$C_{14}$ fatty acid is isopropyl myristate, isopropyl palmitate, isopropyl isostearate, isopropyl linolate or isopropyl monooleate.

The propylene glycol mono- or diester of a $C_8$-$C_{14}$ alkanol or alkenol is propylene glycol monolaurate, propylene glycol monocaprylate or propylene glycol dipelargonate.

The straight or branched $C_8$-$C_{24}$ alkanol or alkenol may be capryl, lauryl, cetyl, stearyl, oleyl, linoyl or myristyl alcohol or 2-octyldodecanol.

The $C_6$-$C_{22}$ acylglyceride is a vegetable oil eg sesame oil, sunflower oil, palm kernel oil, corn oil, safflower oil, olive oil, avocado oil, jojoba oil, grape kernel oil, canola oil, wheat germ oil, almond oil, cottonseed oil, peanut oil, watnut oil or soybean oil, a highly purified vegetable oil eg medium chain triglycerides (caprylic/capric triglycerides), long chain triglycerides, castor oil, caprylic monoglyceride, caprylic/capric mono- and diglycerides or caprylic/capric mono-, di- or triglycerides.

N-alkylpyrrolidone is typically N-methylpyrrolidone and N-alkylpiperidone is typically N-methylpiperidone.

The solubility-improving agent may also be a fatty acid such as a medium, long or very long chain fatty acid including oleic acid and linoleic acid.

The concentration of the solubility improving agent in the electrospun fibres is—if present—in a range of from 0 to about 10% w/w such as from about 0.5 to about 5% w/w.

The thickness of the fibres (they are prepared as a layer) may be varied depending on the intended use. In order to ensure a suitable strength of the fibres, the thickness normally is in a range of from micrometer to about 5 mm. The thickness is like the thickness of paper.

The thickness of the electrospun fibres (which appears as a sheet) is the same throughout the length and width of the sheet. In the present context the term "same" means that the difference in thickness over a length of 1 m and a width of 1 m is at the most 10%.

The bioadhesive substance and the drug substance are homogeneously distributed in the fiber material, which means that the concentration of the substances carried by the fibres (bioadhesive substance, drug substance and optionally the substances/additives mentioned herein) is the same per surface area, wherein the surface area is measured as length× width of a given part of the sheet of fibres Each fibre contains an amount of the bioadhesive substance and the drug substance and, if other additives or ingredients have been employed, such a substance will also be part of the fibres.

The release of the drug substance from the fibres may be immediate release or modified release dependent on the specific drug substance and the intended use. The release rate may be adjusted eg to obtain a slower release by i) use of fibre-forming hydrophilic polymer(s) with an increased average molecular weight,
ii) use of fibre-forming hydrophilic polymer(s) normally intended for use in sustained release compositions or enteric coated compositions,
iii) use of a mixture of fibre-forming hydrophilic polymers, wherein at least one of the polymers is insoluble in water or saliva
iv) increasing the concentration of bioadhesive substance to obtain a more compact fibre upon application to eg the oral cavity, where the bioadhesive substance may cause swellin,
v) increasing the compactness of the network structure in the fibres (alternatively cross-linking of the electrospun fibres,
iii) increasing the thickness,
iv) increasing the fibre diameter,
v) changing manufacturing method (eg from simple needle nozzle to coaxial injection),
vi) applying a further layer eg of hydrophobic material on the fibre layer, which hydrophobic layer is intended to be applied closest to the oral mucosa and thus retarding the release of drug substance from the fibres.

A suitable hydrophobic material that can be used as a backing layer is poly(caprolactone).

Analogous, the release rate may be adjusted eg to obtain a faster release by i) use of fibre-forming hydrophilic polymer(s) with an decreased average molecular weight,
ii) decrease the amount of bioadhesive substance to decrease the compactness of the fibres,
iii) increasing concentration of solubility-improving substance
iv) increase porosity of the fibres,
v) decreasing the thickness of the layer of fibres,
vi) decreasing the compactness of the network structure in the fibres,
vii) increasing concentration of solubility-improving substance,
viii) decreasing the diameter of the fibres,
ix) changing manufacturing method (eg from coaxial injection to simple needle nozzle).

The fibres according to the invention can be used in medicine, notably for the treatment of a disease located to the skin or mucosa.

In a specific aspect, the fibres according to the invention are for use in the treatment of diseases of the oral cavity, notably for local treatment of the oral mucosa.

Such fibres are suitable for use in pharmaceutical compositions for application on the skin or mucosa for the treatment of diseases located to such areas. In the present context the term "mucosa" includes mucosa in the oral cavity, in the vagina, in the rectum, in the eye, in the ear as well as the lips. The fibres are also useful in compositions for application on internal surfaces such as e.g. organs (eg the liver, spleen, heart etc), tissues such as vocal cord, mucosa such as the gastrointestinal mucosa etc. Due to the nature of the electrospun fibres, the compositions of the invention can be provided for immediate release of the drug substance or for controlled release of the drug substance by varying the ingredients employed in the composition or in the electrospun fibres. The electrospun fibres typically become invisible after application, which makes it possible to apply the compositions on any part of the skin or mucosa such as in the face. It is also possible to apply eg cosmetics on the applied composition. This enables good patient compliance as the treatment does not leave any visible signs.

The invention also relates to pharmaceutical compositions comprising the electrospun fibres, to methods for obtaining the electrospun fibres and to use of the electrospun fibres and the pharmaceutical composition in medicine.

The use of electrospun fibres in medicine offer one or more of the following advantages:

i) It is possible to improve the therapeutic effect e.g. designing the compositions as a controlled release composition. In this manner the drug substance is released from the composition over a prolonged period of time and peak concentration of the drug substance at the applied site is avoided; such peak concentrations are very often responsible for un-desired effects such as irritation.

ii) The electrospun fibres are dry, i.e. there is no or only small amounts of water present in the composition. Moreover, the semi-solid compositions that normally are used for treatment of a disease in the skin or mucosa may contain excipients like vegetable oils, waxes, surfactants that may be subject to degradation. Degradation is normally faster if the composition contains a liquid solvent; thus, from a stability perspective, it is an advantage to develop compositions without or with only a minor amount of a solvent present. Accordingly, long shelf-lives are envisaged of the electrospun fibres and compositions of the invention.

iii) The method by which the fibres are electrospun enables fibres to be obtained with a content of more than one drug substance. The different drug substances may be added to the spinning process by injecting one composition containing all drug substances dissolved or dispersed in a solvent in the desired concentrations through one valve, or by using different valves to different drug substance (or a mixture of these two illustrative examples). Another possibility is to provide one layer of fibres containing one drug substance and then on top of this layer provide another layer of fibres containing a second drug substance. Thus, combination products with two or more drug substances can easily be obtained.

iv) The drug substance will be homogeneous distributed in the electrospun fibres; thus, a correct dosing is secured and can be expressed e.g. as amount drug substance per surface area.

v) The electrospun fibres and compositions are highly skin or mucosa friendly; the fibres become transparent upon application and cosmetics can be applied on top of the fibres/compositions.

vi) The electrospun fibres/compositions are easy to apply. Normally, the composition contains three layers: a release-liner layer, a layer containing the electrospun fibres, and, optionally, a backing layer. The release liner layer serves as a protective layer for the drug-containing layer and is to be removed before application. The backing layer can be regarded as a coating that protects the composition from being removed from the application site (eg in the oral cavity by movements of the tongue or presence of saliva) or as an occlusive layer that drives the release of the active substance to the skin or mucosa.

vii) In contrast to compositions normally used to treat diseases of the skin or mucosa, the electrospun fibres and compositions of the invention do not smell.

viii) The electronspun fibres and compositions of the invention do not contain any or any substantial amount of alcohol or surfactants. The presence of such substances in topical or mucosal compositions often leads to irritation of the skin or mucosa.

ix) The electrospun fibres and compositions of the invention do not contain any preservatives.

However, it is contemplates that other methods such as other methods involving electrostatic forces may be used to obtain equal results. The overall term for such methods is electrohydrodynamic (EHD) methods and includes electrospinning, electrospraying, coaxial electrospinning, coaxial electrospraying, emulsion electrospinning, etc. Such methods are intended to be part of the present invention in relation to preparation of the fibres according to the invention.

Pharmaceutical Compositions

As mentioned herein, the present invention also provides pharmaceutical compositions comprising the electrospun fibres described herein.

The pharmaceutical compositions are intended for use on the skin or on a mucosal surface, notably a mucosal surface of the oral cavity. A composition of the invention is typically in the form of a sheet containing one of more layers, where at least one layer contains the electrospun fibres and wherein the electrospun fibres contain the drug substance. The composition may be provided in the form of a sheet. It may be have a round, elongated or polygonal shape. The composition or the invention is a dosage form, which could be denoted sheet, layered composition, membrane, or patch.

In a simple form the composition only contains one layer, namely the layer of drug-containing electrospun fibres. Such a composition is suitable for use on the skin. After application the composition stays on the application site due to its bioadhesive character and it becomes transparent.

The composition may also contain more than one layer such as two or three or more layers. If the composition for example contains two layers, each layer may be a layer of drug-containing electrospun fibres, where the drug substance in the two layers may be the same or different. The two layers may also have different composition with respect to nature and content of fibre-forming hydrophilic polymers and/or bioadhesive substances in order to facilitate a different release pattern of the drug substance from the two different layers. Another example is that the composition contains one or more layer(s) of drug-containing electrospun fibres and another therapeutically inert layer, which functions as a backing layer to protect the drug-containing layer(s) from moisture or saliva or to function as an occlusive layer, which may drive the penetration of the drug substance into the skin or mucosa. In case, where such a composition is applied to the oral mucosa, a backing layer protects the drug-layer from being washed away from the application site, which would result in swallowing of the composition, whereby the desired local therapeutic effect is reduced or eliminated.

Alternatively, the composition may contain a layer, wherein a specific area is made up of one type of electrospun fibres and another specific area is made up of another type of electrospun fibres.

In some case it may be desired to have one or more layers of electrospun fibres without any content of a drug substance between the layer(s) of drug-containing electrospun fibres and/or a backing layer. Such layers of electrospun fibres may have the same composition as the layer of drug-containing electrospun fibres, but without any content of drug substance, or the composition may be different eg containing a fibre-forming hydrophobic polymer or a mixture of a hydrophobic and fibre-forming hydrophilic polymer. It is envisaged that such a layer may be used to adjust the release of the drug substance from the composition. Thus, such a composition is of particular interest in the case where a controlled release composition is desired. In this manner it is contemplated that an improved ratio between side effects and clinical effect can be obtained, i.e. it is possible to reduce the unwanted effects and at the same time achieve a therapeutically effective response.

The backing layer is typically either co-spun with the drug-containing layer or it is provided as a coating layer on top of a drug-containing layer. Typically, the backing layer is water-impermeable to enable an occlusive effect and/or a protective effect against eg saliva. Suitable materials for backing layer include polyethylene-co-vinyl acetate, ethylcellulose, poly(caprolactone), carbothane or polysoftane. Moreover, materials such as actylates/octylacrylamide copolymer (sold under the name DERMACRL® 79), amino methacrylate copolymer (EUDRAGIT®), dimethylaminoethyl methacrylate, methacrylate, methyl methacrylate (e.g. EUDRAGIT®E 100) and other acrylates may be used or added. Plasticizers like those mentioned herein before (e.g. tributyl citrate) can also be added.

The backing layer, if present, normally has a thickness in the same order of magnitude as the composition. The backing layer, if present, normally make up about 30-60% w/w of the composition.

The composition may be subjected to heat treatment in order to melt the substance contained in the backing layer. The effect thereof is to obtain a closer structure of the backing layer in order to avoid penetration of water (or saliva or another relevant body fluid) into the composition and thereby avoiding the risk of releasing the drug substance too fast or avoiding the risk of unwanted separation of the backing layer from the drug-containing layer. The temperature employed should be a balance between obtaining melting of the substance in the backing layer and avoiding unwanted degradation of the drug substance. Poly(caprolactone) melts at about 65° C.

A composition of the invention may be provided with a release liner layer. This layer is not part of the composition and is an inert layer, which must be removed before application on the skin or mucosa. The release liner layer only serves a practical purpose as it is difficult to handle and to pack a sheet of electrospun fibres without protecting the composition from the environment. Thus, if the composition only contains one layer, i.e. the layer of drug-containing electrospun fibres, it may be provided with a release liner layer both on the two outermost surfaces of the layer The electronspun fibres and/or the compositions containing the fibres may also contain one or more pharmaceutically acceptable excipients, some of which have already been disclosed herein and they can also be added to a composition of the invention so that they are part of the composition, but not contained inside the electrospun fibres.

Such excipients (which also may be used in the preparation of the electrospun fibres) include taste-masking agents such as aromas or sweetening agents; pH adjusting agents such as buffer substances like citrates, acetate, or phosphate;

release modifiers; pore-forming agent, stabilizing agents; anti-oxidants; pigments; skin conditioning agents including urea, glycerol etc, anti-irritative agents such as glycerol, menthol, eucalyptol or nicotinamide; anti-nucleating agents such as glycerol; penetration enhancers such as azone, N-methylpyrrolidone, propylene glycol etc.

The release of the drug substance from the composition may be immediate or modified dependent on the particular drug substance employed and the intended use. The release rate may be adjusted as described herein before under the heading "Electrospun fibres", and/or it may be adjusted by use of specific pharmaceutically acceptable excipient.

A faster release may be obtained by use of penetration enhancer and/or by inclusion of a plasticizer.

A composition of the invention suitable for use on the skin or mucosa is typically composed of
i) from about 75-100% w/w of the drug-containing electrospun fibres
ii) from about 0-25% w/w of one or more pharmaceutically acceptable excipients (as described herein), A composition of the invention suitable for use on the skin or mucosa is typically composed of
i) from about 50-70% w/w of the drug-containing electrospun fibres
ii) from about t 0-10% w/w of one or more pharmaceutically acceptable excipients (as described herein), and
iii) from about 30 to 50% w/w of a backing layer.

Method for Preparing Fibres According to the Invention

The present invention also provides methods for preparing electrospun fibres.

A first method comprising
i) dissolving the hydrophilic polymer in a first solvent,
ii) suspending the bioadhesive substance in the resulting solution from step i)
iii) optionally, adding a drug substance to the resulting dispersion from step ii)
iv) electrospinning the resulting mixture from step ii) or iii), wherein said hydrophilic polymer is soluble in said first solvent, and said bioadhesive substance is slightly soluble or less in said first solvent,
to obtain electrospun fibres, wherein at least 90% w/w of the bioadhesive substance is present in undissolved form.

An alternative method for preparing electrospun fibres according to the invention comprises the steps of
i) dissolving the hydrophilic polymer in a first solvent to obtain a first solution,
ii) optionally, dissolving or suspending a drug substance in said first solution to obtain a first mixture,
iii) suspending the bioadhesive substance in the first solvent to obtain a second dispersion,
iiv) dual-electrospinning the first solution (or first mixture if a drug substance is included) and the second dispersion, wherein said hydrophilic polymer is soluble in said first solvent, and said bioadhesive substance is slightly soluble in said first solvent,
to obtain electrospun fibres, wherein at least 90% w/w of the bioadhesive substance is present in undissolved form.

As mentioned hereinbefore a suitable solvent is one or more volatile solvents, notably a $C_1$-$C_3$ alkanol such as ethanol or ethanol-water mixtures. Water may be present up to about 20% v/v notably from about 3 to about 10% v/v. In those cases where the fibre-forming hydrophilic polymer and the bioadhesive substance are spun by dual-electrospinning, i.e. from two separate syringes, water may be used in concentrations up to about 60% v/v, notably up to about 50% v/v or up to about 40% v/v. In such cases the solvent for the fibre-forming hydrophilic polymer and the bioadhesive substance is not the same as the solvent used for the bioadhesive substance must be a solvent in which the bioadhesive substance is only slightly soluble or less than slightly soluble. A suitable solvent in which the bioadhesive substance is not soluble is notably ethanol or ethanol-water mixtures with a water content up to about 20% v/v, notable from about 3 to about 10% v/v.

The concentration of the fibre-forming hydrophilic polymer in the first solvent is typically in a range of from about 2 to about 40% w/w, notably from about 3 to about 30% w/w.

The concentration of the bioadhesive substance in the first solvent or in the second dispersion is typically from about 1 to about 20% w/w notably from about 1 to about 15% w/w.

The methods mentioned above may include a final step of coating an outer surface of the fibres with a hydrophobic polymer.

The coating may be in form of spraying, film casting, electrospinning etc.

After coating, the coated fibres may be subject to heating to melt or soften the hydrophobic polymer in order to obtain a more closed structure of the hydrophobic polymer.

The present invention also relates to a kit as described in the claims. Use in medicine The drug-containing electrospun fibres and the compositions containing the drug-containing electrospun fibres are suitable for use in medicine.

As mentioned above, the drug-containing electrospun fibres and compositions are primarily intended for local administration to a diseased site on the skin or on a mucosa. However, it is envisaged that a person skilled in the art and based on the present disclosure will be able to utilize the concept of present invention to obtain compositions that enable delivery to the systemic circulation after administration to the skin or mucosa or compositions that enable delivery of the drug substance to a body cavity such as the oral cavity. However, the object of the present invention is to provide electrospun fibres and compositions that stay on the diseased tissue to obtain a local effect.

Drug substances suitable for use in connection with the present invention may be drug substances that are small molecules or it may be peptides, proteins, biologics including mono- or polyclonal antibodies.

Skin Diseases

Examples of skin diseases are actinic keratosis, skin cancers (basal cell carcinoma, Bowen's disease, squamous cell carcinoma, and malignant melanomas), genital warts, acne, dermatitis, psoriasis, rosacea, ichtyoisis, eczema, atopic dermatitis, puritus, pustolis palmophantatis, pain, infections, viral diseases such as herpes.

Today some of these skin diseases (actinic keratosis, skin cancers (basal cell carcinoma, Bowen's disease, squamous cell carcinoma, and malignant melanomas), genital warts) may be treated with imiquimod, which is a prescription medication that acts as an immune response modifier. It has also been suggest to be used in the treatment of vulvar intraepithelial neoplasia, vaginal intraepithelial neoplasia, and common warts. However, there are several adverse effects of the treatment such as blisteres, bloody dry eschar, pain and general discomfort. Moreover, many of the patients cannot tolerate the treatment.

Another treatment of actinic keratosis is ingenol.

A gel containing ingenol mebutate is on the market today in two different strengths for use on either the face and scalp (0.015%) or the trunk and extremities (0.05%), respectively. Clinical studies have shown has ingenol mebutate gel applied topically for 2 to 3 days is effective for field treatment of actinic keratosis.

Ingenol mebutate is sold under the name Picato®. The substance is an ester of the diterpene ingenol and angelic acid. Ingenol mebutate is practically not absorbed through the skin.

However, application of the gel very often leads to irritations of the application site. This includes redness, scaling, crusting, pain, and sometimes infection. Other side-effects include eye irritation such as periorbital edema, headache and nasophyryngitis.

Due to the common side-effect of irritation of the application site there is a need for developing a composition containing ingenol mebutate or another ingenol derivative which upon application to the skin is less irritative than the known composition. Moreover, a composition of the invention containing eg ingenol mebutate or imiquimod and being in the form of a sheet with a well-defined area (i.e. it contains the desired dose of the drug substance) may have improved long term and less recurrence due to correct dosing at every application.

A composition suitable for use typically comprises electrospun fibres, wherein the fibres are based on PVP and additionally contains a fibre-forming agent, a plasticizer, an anti-irritative agent and the drug substance. When imiquimod is the drug substance it may be present in the fibres as a dispersion or a solution, where e.g. oleic acid is used as a solvent. A typical example of a hydrophilic fibre-forming agent is an acrylate (eg as described herein) or PVP. The plasticizer may be tributyl citrate and the anti-irritative agent may be glycerol.

Other drug substances used in the treatment of skin diseases and suitable for use in accordance with the present invention are vitamin D derivatives or analogues, corticosteroids, phosphodiesterase 4 inhibitors, ingenol derivatives, retinol such as adaplene, JAK inhibitors, NK-1 receptor antagonists, calcineurin inhibitors such as tacrolimus or picrolimus, keratolytic agents such as salicylic acid or lactic acid, antibiotics such as fucidic acid, bactoban, or clindamycin, non-steriodal antiinflammatory agents such as diclofenac, naproxene, ibuprofen, ketoprofen, anti-neoplastic agents such as 5-fluoracil, local anesthetics such as lidocain, prilocain etc.

Diseases of Mucosa, Notably the Lips and Oral Cavity

Diseases of the oral cavity that can be treated with the electrospun fibres or compositions of the invention include:

Inflammatory conditions such as oral lichen planus and mouth ulcers. Such conditions are normally treated with corticosteroids. The corticosteroid may be selected from the group consisting of amcinonide, betamethasone, budenoside, clobetasol, clobetasone, cortisone, desonide, desoxycortisone, desoximethasone, dexamethasone, diflucorto-Ion, diflorasone, flucortisone, flumethasone, flunisolide, fluocinonide, fluocinolon, fluorometholone, fluprednisolone, flurandrenolide, fluticasone, halcinonide, halobetasol, hydrocortisone, meprednisone, methylprednisone, mometasone, paramethasone, prednicarbate, prednisone, prednisolone and triamcinolone or a pharmaceutically acceptable ester or acetonide thereof. The corticosteroid may preferably be selected from betamethasone, budenoside, clobetasol, clobetasone, desoximethasone, diflucortolon, diflorasone, fluocinonide, fluocinolon, halcinonide, halobetasol, hydrocortisone, mometasone and triamcinolone or a pharmaceutically acceptable ester thereof. The corticosteroid ester may for instance be betamethasone acetate, betamethasone dipropionate, betamethasone valerate, elobetasol propionate, dexamethasone acetate, flumethasone pivalate, fluticasone propionate, hydrocortisone acetate, hydrocortisone butyrate or mometasone furoate. The acetonide may be selected from fluocinolone acetonide or triamcinolone acetonide. The corticosteroid is preferably betamethasone dipropionate or betamethasone valerate.

Pain conditions (treatment with analgesics such as NSAIDs—ibuprofen, ketoprofen, diclofenc etc.).

Fungal diseases (treatment with metronidazole, ketoconazole etc.).

Viral diseases such as herpes simplex (treatment with acyclovir).

Various dysplasia conditions (treatment with 5-fluoruracil, diclofenac, retinoids, ingenol mebutate).

In the following is given a more specific description of the clinical applications for treatment of oral diseases.

Use as Simple Wound Dressings (with or without Incorporated Drugs)

(a) Oral Ulceration

The oral mucosa is frequently traumatised during mastication and as the result thermal, chemical and physical injury. This usually leads to ulceration of the oral mucosa. The ulcerated area is painful, very sensitive to touch, hot foods and drinks, alcohol and strong or spicy flavours. This can be very uncomfortable and make eating, drinking and speech difficult. In addition, around 25% of the population experience recurrent episodes of oral ulceration (known as aphthous ulceration) at some point during their lives. They experience one or several mouth ulcers at a time that develop spontaneously, last a few days to a few weeks and then heal by themselves. These crops of ulcers recur frequently.

As with a wound to the skin, there is a natural instinct to cover such wounds in the mouth. Unfortunately, the equivalent of a Band-Aid does not yet exist for the mouth. Thin and flexible electrospun compositions that adhere to the oral mucosa and provide a degree of protection to the wound from the spicy foods, strong flavours etc that pass through the mouth as well as providing a degree of protection from bacterial contamination and physical trauma would speed wound healing and provide relief from the discomfort associated with oral ulcers. Ideally, these compositions should resorb slowly over a few days so that removal is not necessary. Healing of protected wounds in the mouth is generally very fast.

In some cases it is relevant to use electrospun fibres without any content of drug substance and, thus, the present invention also relates to such electrospun fibres (as described in detail herein, but without any content of drug substance), to compositions comprising the electrospun fibres and to the use of the fibres and compositions in medicine, i.e. not only to the above-mentioned appliance.

(b) Wound Dressing Following Surgery

Surgical procedures in the mouth, particularly extractions, are more common than any other form of surgical procedure. Currently, following a simple tooth extraction, the open socket is left unprotected to form a blood clot and heal by itself. Fortunately, healing in the mouth is very effective, None-the-less, post extraction haemorrhage is common—often due the blood clot being dislodged, infection of the tooth socket—leading to delay in wound healing or the very painful condition of 'dry socket', is also common. Patients also dislike the sensation of an open socket in the mouth and the associated taste of blood. Covering the extraction socket with an adhesive electrospun composition eg in the form of a dressing, would help to keep the forming blood clot in place and so reduce post-extraction haemorrhage and improve wound healing. It would also reduce infection and the entry of food debris into the socket again facilitating wound healing and reducing wound infection. As well as physically covering the open socket providing comfort and reassurance to the patient. Such compositions would require good adhesion, need to have good strength, low permeability and ideally to stay in place for the first 24 hours while the blood clot stabilises.

As well as extractions many other surgical procedures are performed in the mouth, including, biopsies, gingival surgery, surgical extractions, implant surgery, orthodontic surgery etc. All leave open wounds or areas of suturing where suitable wound dressings would help reduce wound infection and secondary haemorrhage as well as providing physical protection and comfort for the patient.

(c) Active Wound Dressings

Although physical protection alone would have considerable benefit, the incorporation of drugs and other active agents in some wound dressings would have particular value in specific situations:

(i) Antiseptics. As secondary infection is a common issue with oral wounds, the incorporation and slow release of a well-tolerated antiseptic agent such as chlorhexidine gluconate or cetylpyridinium chloride (used in antiseptic mouthwashes) could be of value in situation where secondary infection is a particular issue.

(ii) Analgesics. Most oral ulcers are associated with pain and inflammation so the incorporation and slow release of a well-established topical analgesic/antiinflammatory agent such as benzydamine hydrochloride could provide pain relief and a soothing effect as well as physical coverage.

(iii) Haemostatic. Post extraction haemorrhage is a common problem of concern to dentists and patients. Where haemorrhage is difficult to control with simple measures such as direct pressure. In such situations dentists and oral surgeons often use tranexamic acid—which inhibits fibrinolysis. However, because it comes in a tablet form it is difficult to apply locally to the tooth socket and so its main effect is systemic. Release of tranexamic acid from a socket covering composition eg in the form of a sheet or patch would physically prevent/reduce haemorrhage as well as preventing fibrinolysis locally in the socket whilst minimising the likelihood of any systemic effect. The composition would amplify the local effect of transexamic acid by preventing its loss from the socket.

Actinic Keratosis and Oral Leukoplakia

Actinic Keratosis (Solar Keratosis) is UV light induced premalignant lesion of the lip that has a significant risk of developing into a lip cancer. Such lesions are often surgically excised or treated with cryotherapy but recently the application of Imiquimod (Aldara), diclofenac (Solaraze) and Fluorouracil (Efudix) creams has been shown to be of benefit in treating some cases of actinic keratosis. However, better methods of retaining, localising and slowly releasing the active agents are needed than is achieved with the creams. Thus there is an interest in incorporating these drugs into electrospun compositions that can cover the area of actinic keratosis and slowly release the active agent for improved treatment.

Oral leukoplakia is a potentially malignant lesion of the oral mucosa that has a significant risk of converting to oral cancer. Oral leukoplakias are more common than actinic keratosis and occur more frequently in smokers. Their potential for malignant change is usually assessed by taking a biopsy of the lesion. A histopathologist then grades the degree of dysplasia in the lesion. Those lesions exhibiting moderate or severe dysplasia are considered at high risk of progressing to cancer. Current treatment of oral dysplastic lesion involves risk reduction e.g. stopping smoking and if the lesion is considered at high risk then surgical excision. Since oral leukoplakias can be extensive and it is difficult to access regions of the mouth, surgical treatment can be difficult and may be mutilating and unpleasant for the patient often leaving residual morbidity. Moreover, surgical removal may not reduce the risk of an oral cancer developing. Attempts have been made to use Imiquimod (Aldara), diclofenac (Solaraze) and Fluorouracil (Efudix) creams to treat oral leukoplakias. However, the presence of saliva make application and retention of the creams difficult and the large size of many oral leukoplakias and the risk of swallowing the drug compound the difficulties as well as significantly increasing the risk of systemic side effects from the drugs. Localised, slow release delivery via a bioadhesive electrospun composition of the invention, directly to the lesion would solve many of these problems particularly if the composition has an impermeable backing to ensure unidirectional delivery of the drug into the lesion and not into the oral cavity where it could be swallowed.

'Cold Sores'

Between 40% and 70% of the population (depending on geographic area and socioeconomic group) are latently infected with the herpes simplex type 1 virus. Of these, 20-40% experience periods of reactivation of the virus which most commonly presents as cold sores. In many individuals, cold sores are a common and reoccurring problem. Most often they are present as a crop of vesicles (small blisters) at the junction of the lip and the surrounding skin. These then rupture to form small ulcers that exude fluid and then crust over before healing spontaneously over 7 to 10 days. They cause considerable, pain, discomfort and embarrassment. If treated with topical antiviral agents such as acyclovir (Zovirax) or Penciclovir (Vectavir) cream at the earliest stages of lesion development the duration and severity of episodes can be reduced. However, the cream needs to be applied very frequently (respectively 5× daily and 2 hourly) to be effective and does nothing to provide coverage to prevent secondary infection or hide the appearance of the lesions. Small electrospun skin adhesive compositions delivering slow release acyclovir or a similar antiviral agent, would be more effect and would also provide coverage to hide the lesions and prevent secondary infection.

Less commonly, cold sores form small, localised crops of blisters and ulcers on the lining mucosa of the mouth, most often the roof of the mouth. Again these are very painful but much more difficult to apply an anti-viral cream to. With appropriate formulation in accordance with the present invention, a composition of the invention can used to treat cold sores on the lips could also be used to treat lesions within the mouth Treatment of Immunologically Mediated Oral Mucosal Disease There are several common immunological mediated oral mucosal diseases that result in extensive areas of oral mucosal erosion (thinning) and ulceration. Wherever there is thinning or ulceration of the oral mucosa it is painful, very sensitive to touch, hot foods and drinks, alcohol and strong or spicy flavours. This can be extremely uncomfortable and make eating, drinking and speech difficult. As previously discussed, simple coverage of such areas can provide considerable relief. However, these conditions are either recurrent—such as recurrent aphthous stomatitis, or chronic. Therefore, suppression of the underlying disease process is essential if lesion improvement is to occur with long-term improvements for the patient.

Many of these conditions are susceptible to immunomodulatory drugs such as steroids, cyclosporine and mycophenelate mofetil. Generally steroids are the first line of therapy but there are virtually none formulated for topical drug delivery to lesions in the mouth, particularly as creams and ointments will not adhere to the oral mucosa and therefore easily swallowed and have virtually no duration of action where needed. As a result, steroid tablets (prednisolone and betamethasone valerate) are dissolved in water to make mouthwashes or steroid inhalers are directed at affected areas of oral mucosa. However, the contact time of drugs delivered in this way to oral lesions is extremely short and so high doses, high potency steroids and frequent application is required to compensate for this. In turn this increases the risk of both oral and systemic side effects. Indeed, for more severe and difficult to treat lesions it is often necessary to resort to the use of systemic steroids to treat a localised disease. Even then, many patients area resistant to treatment and it is often necessary to turn to more potent or steroid sparing alternative immunomodulatory drugs such as azathioprine, cyclosporine and mycophenelate mofetil. Again there are no topical oral preparations of these drugs so they frequently have to be used systemically.

Because the oral lesions are superficial and easily accessible modern biological agents such as antibodies and kinase inhibitors that often have to be given parenterally (by injection) could be applied directly to the lesion and have an effect if they were available in a suitable delivery system.

Thus electrospun bioadhesive compositions in accordance with the present invention providing uni-directional drug delivery into the lesion would provide much needed and effective treatment of a wide range of oral mucosal diseases. In terms of the most widely applicable drug to incorporate into a sheet a steroid preparation would be the best starting place. Hydrocortisone has the benefit of no significant absorption from the gut. In general it is of too low potency to be effective for oral mucosal diseases but with longer retention times and slow release it may well prove effective when delivered from a uni-directional patch. Stronger steroid preparations however, are widely used including trimacinolone acetonide—that has a proven track record as a topically delivered medium potency steroid (used to be available as triamcinolone in OROBASE® for topical delivery to oral lesions—but is no longer available). Otherwise betamethasone or fluocinolone have increasing potency and are widely used for treating oral mucosal disease currently. While steroids and other immunomodulatory drugs suppress the underlying disease process they are not effective at providing immediate symptomatic pain relief. Therefore a combined steroid and topical analgesic/antiinflammatory (benzidamine hydrochloride) drug delivery membrane could be of particular value.

Specific oral mucosal diseases suitable to being treated with a composition in accordance with the present invention include:
(i) Recurrent aphtous stomatitis—as previously described
(ii) Oral lichen planus (OLP)—This condition affects 1.5-2% of the population. Unlike the skin form of lichen planus, Oral lichen planus once established lasts for many years, causes far more painful lesions and is much more resistant to treatment. Patients get widespread erosions and ulceration that affects mainly the buccal mucosa (inside the cheeks), the sides of the tongue and the gums that are often painful and extremely sensitive to foods etc.
(iii) Pemphigoid—this is a group of blistering conditions that can affect the skin and mucous membranes. It is caused by auto-antibodies damaging the junction between the epithelium and the underlying connective tissue so that the epithelium splits from the underlying tissue. The oral mucosa is invariably affected producing large blisters that break down to form extensive areas of oral ulceration. The gums are widely affected but ulcers can also develop on the roof of the mouth tongue and inside the cheeks. It is somewhat less common the OLP.
(iv) Pemphigus—this is another blistering condition affecting the skin and mucous membranes. It is slightly different to pemphigus in that autoantibodies damage the junctions that bond epithelial cells to each other. Again the oral mucosa is invariably affected. Although it is slightly less common than pemphigus it is generally more severe and difficult to treat often necessitating the use of systemic steroids and immunomodulatory drugs. However, the use of electrospun mucoadhesive membranes that uni-directionally deliver potent steroids in a slow release fashion would likely preclude the necessity to deliver these drugs systemically.

Delivery of Local Anaesthetics

Local anaesthetics are used widely eg within dentistry. In order to deliver sufficient local anaesthesia for tooth extraction it is usually necessary to give it by nerve block injection or local infiltration injection. Because the injection itself is painful it is not uncommon to first apply topical local anaesthetic gel to the oral mucosa at the intended site of injection. This is frequently done for children and apprehensive patients. Unfortunately, the gel often makes poor contact with the mucosa so that local anaesthetic penetration is poor and most of the gel becomes dissipated in the mouth. This causes unpleasant numbness around the mouth and also has a very bitter and unpleasant taste. As a result the procedure is often of limited effect. Topical delivery of local anaesthetic via a uni-directional, bioadhesive, electrospun composition (eg a drug delivery patch) would result in better localisation and penetration of the local anaesthetic, and thus better efficacy, as well as limiting the adverse effects of widespread numbness and bad taste. The composition would only need a short attachment time or if sterile could be left in place and the injection given through the composition.

An effective bioadhesive, local anaesthetic composition eg in the form of a drug delivery patch, could potentially provide sufficient analgesia for many types of routine dentistry on upper teeth—where infiltration local anaesthesia is usually given, or where procedures are relatively minor.

Local anaesthetic is also extensively used in the mouth for soft tissue surgery including gingival surgery, biopsies etc. Again infiltration anaesthesia is usually given in these situations and it is likely that efficient local anaesthesia could be obtained in these situations, because bone penetration of the local anaesthetic agent is not required, simply by using a uni-directional, bioadhesive, electrospun local anaesthetic drug composition.

The most obvious local anaesthetic to use in this situation would be lignocaine (lidocaine) hydrochloride although articaine would be a possible alternative. The incorporation of adrenaline as occurs in many local anaesthetic injection solutions may be beneficial in causing local vasoconstriction and thereby enhancing and prolonging the effect of the local anaesthetic agent.

Treatment of Oral Mucositis

Radiotherapy and chemotherapy for cancers are associated with serious side effects. One of the worst is the oral mucositis that occurs. This results in extensive sloughing and ulceration of the oral mucosa. The resulting pain and discomfort often makes eating and drinking impossible and requires the use of narcotic analgesics. Frequently, the cancer treatment has to be abandoned or reduced because of the severity and distress caused by oral mucositis. Currently there is no effective preventative or curative measures. However, the use of bioadhesive wound dressings in accordance with the present invention as discussed above would be helpful in their own right but the inclusion of a local analgesic e.g. benzidamine hydrochloride could be even more effective at alleviating pain. Benzidamine hydrochloride mouthwashes do provide symptomatic relief but their effect is very short lived. This could be extended and enhance by a composition of the invention, which provides uni-directional delivery to the affected mucosa from the composition eg in the form of a drug delivery patch.

Also recent research has shown that the use of an adrenaline mouthwash before radio- or chemotherapy treatment sessions can help prevent oral mucositis. This appears to be because the vasoconstriction induced in the subepithelial blood vessels by the adrenaline reduces the toxic bystander effects of the treatment on the oral mucosa. Unfortunately, the short contact time with the mucosa that occurs with mouthwash delivery and indiscriminate application to all mucosal sites means that drug delivery is inefficient and systemic side effects of the adrenaline more likely. More direct, prolonged and sustained release of adrenaline into susceptible oral mucosal sites using a composition in accordance with the present invention eg a uni-directional, bioadhesive, electrospun drug delivery patch or membrane delivery system would be far more efficient and effective.

Delivery of Drugs into the Oral Cavity

Instead of using electrospun compositions (eg in the form of membranes or patches) to deliver drugs uni-directionally into the oral mucosa to which they are attached as a wound dressing, it is also possible to design composition that adhere to the oral mucosa but deliver drugs into the oral cavity. These can be used to treat more widespread problems in the mouth e.g. oral candidiasis or to slowly deliver drugs to the throat, oesophagus and upper GI tract.

The main advantage of such systems is the ability of the composition (eg in the form of a membrane or a patch) to act as a drug reservoir and slowly but continuously release the drug into the mouth.

(i) Oral candidiasis. This is a common fungal infection of the mouth. It is particularly common in those who wear dentures, those who smoke or have a high sugar intake, those with diabetes or are immunocompromised and those who are taking antibiotics or immunosuppressant treatments including steroids. There are several antifungal drugs that would be effective and safe for treating oral fungal infections (although several are no longer available as oral preparations). However, they all need frequent application because they are rapidly lost from the oral cavity due to swallowing. The main advantage of a composition in accordance with the present invention (eg in the form of a membrane or a patch delivery system) would be the possibility of providing a slow and continual release of drug into the oral cavity. The drugs likely to be most effective and safe would be nystatin and amphotericin. Although the azole antifungals are very effective the risk of systemic absorption and the potential to interact with other drugs means they are likely to have a worse safety profile.

(ii) Drugs can also be delivered to the throat e.g. antiseptics, analgesics and local anaesthetics for treating sore throats colds etc. or to the oesophagus and stomach e.g. antacids, proton pump inhibitors etc or even systemically via the GI tract. The main advantage being the possibility for slow and continuous drug delivery.

Systemic Delivery of Drugs Across the Oral Mucosa

Although the electrospun fibres and compositions according to the invention primarily are intended for local treatment of the skin or mucosa, it is contemplated that electrospun fibres or compositions made in accordance with the present invention but comprising a drug substance that is intended for delivery into the systemic circulation may be suitable for application to the oral mucosa, but for systemic administration through the oral mucosa.

The oral mucosa is readily accessible is more permeable than skin and better supplied with blood vessels. It also has the advantage that drugs delivered across the oral mucosa and into the circulation avoid the problem of first pass metabolism in the liver. This means that drugs that need rapid administration, including some emergency drugs, and some drugs that would otherwise need to be delivered by injection or would be inactivated in the liver can be more effectively administered across the oral mucosa. Electrospun adhesive drug delivery compositions that uni-directionally deliver such drugs across the oral mucosa can be very effective. They can be used to deliver emergency drugs in the unconscious patients or where injections not possible e.g. where suitably trained staff are not available.

(i) Emergency drug administration: Drugs commonly delivered across the oral mucosa include:

a. Glyceryl trinitrate—This is usually given in the form of a sublingual (under the tongue) spray or quickly dissolving tablet to treat episodes of angina (chest pains). However, the speed of delivery is such that it often causes very severe headache due to the over quick dilatation of cerebral as well as cardiac blood vessels and may need to be repeated several times. Transmucosal delivery of glyceryl trinitrate in a more controlled fashion from a bioadhesive composition eg in the form of a membrane or a patch could produce a smoother and longer duration of dosage and avoid such problems.

b. Aspirin—is often delivered across the oral mucosa in heart attack and stroke patients, particularly when unconscious, in order to reduce thrombosis and worsening of the condition. This usually achieved by placing a soluble aspirin tablet in the buccal sulcus (between the gums and the inside of the cheek) and allowing it to dissolve. However, much of the drug is lost into the oral cavity rather than accurately delivered across the oral mucosa. Again a more controlled, more directed and longer duration of trans-mucosal delivery could be achieved using the formulation principle in accordance with the present invention, eg in the form of a a bioadhesive electrospun drug delivery patch.

c. Midazolam—is very effective at halting epileptic fits, particularly when they are prolonged or recurring. Although normally given by intravenous injection, this can be very difficult in a fitting patient. So more recently it has been recommended that midazolam solution is simply placed between the cheek and the gums or under the tongue as it rapidly crosses the oral mucosa to enter the circulation and abort fitting. Delivery by this route is uncertain with much of the drug being lost or swallowed. Again a more controlled, more directed and longer duration of transmucosal delivery could be achieved using a composition in accordance with the present invention eg as a bioadhesive electrospun drug delivery patch.

(ii) Delivery of narcotic analgesics. Narcotic (opioid) analgesics are widely used for the treatment of severe and intractable pain particularly cancer related pain and for management of post-operative and trauma related pain (including battlefield injuries). The main problem is that most opioid analgesics need to be given by injection with frequent repeat doses by injection because they are rapidly metabolised in the liver. Some opioid analgesics are now available in patch form for transdermal delivery or sprays for trans nasal delivery but trans mucosal delivery via electrospun bioadhesive oral compositions, eg patches, offers considerable advantages. Including, slower, more controlled and more sustained drug delivery. More effective drug penetration into the circulation than with skin patches as well as the avoidance of first pass metabolism in the liver. Drugs likely to provide good candidates for this approach include: morphine, pethidine, buprenorphine and fentanyl.

MATERIALS

The following materials are used in the experiments reported in the Examples below.
Polyvidone 90.000 (Kollidone 90K) is obtained from BASF, Germany
Klucel LF is obtained from Hercules Incorporated, US
Eudragit E, is obtained from Evonik Industires
Eudragit RS, Evonik Industires
Dermacryl 79, is obtained from AkzoNobel
Tributyl citrate, Ethanol, Sodium acetate, Hydrochloric acid & Bethamethasone dipropionate and clobetasol propionate are obtained from Sigma-Aldrich
Dextran, Molecular weight 500.000, 750.000, 1.000.000 are obtained from Pharmacosmos Denmark
Polyethylene oxide 400.000, 2.000.000, 4.000.000 are obtained from The Dow Chemical Company
Medium chain glyceride, Henry Lamotte Oils GmbH
Imiquimod and clobetasol propionate are obtained from APIChem Technology Co., Ltd.
Carbothane is obtained from Lubrizol Corporation US
Methods
Analysis of Bethamethasone dipropionate or clobetasol propionate by HPLC:
Column: Sunfire C18; 3.5 μm or 5 μm; 150×4.6 mm ID or equivalent
Mobile Phase: Acetonitrile/0.01 M $(NH_4)_2HPO_4$ pH 6.4, 70:30 (v/v).
Flow rate: 0.8 ml/min
Detection Wavelength: 240 nm
Analysis of Imiquimod by HPLC:
Column: Phenomenex $C_{18}$ column or equivalent
Mobile phase: 40:60 Acetonitril to water containing 1% trifluoroacetic acid
Flow rate: 1 ml/min
Detection wavelength: 242 nm

EXAMPLES

Example 1

Preparation of Alcoholic Gel Ready for Electrospinning—Dextran as Bioadhesive Substance

| Fibre-forming hydrophilic polymer | Bioadhesive substance | | | Solvent Ethanol |
|---|---|---|---|---|
| | Dextran[1] 500.000 | Dextran[1] 750.000 | Dextran[1] 2.000.000 | |
| Polyvidone Kollindon 90F10% | x | x | x | x | x |
| Klucel LF 5%(HPC) | x | | X | | x |
| Eudragit E 15% | x | | X | | X |
| Eudragit RS 15% | x | x | X | x | X |
| Dermacryl 79 10% | x | | x | | X |

1) The content of the different dextrans varied between 2.5, 5.0 and 7.5% by weight of the gel or between 25 to 75% by weight of the fibre-forming hydrophilic polymer in those cases where PVP or Dermacryl was used. Experiments have shown that it is possible to use at least up 20% w/w of dextran. The weight ratios between the bioadhesive substance and the hydrophilic polymer are 0.1 to 1.5, namely 0.1, 0.16, 0.25, 0.33, 0.5, 0.75, 1, 1.5.

To prepare the gels, dextrans were suspended in the ethanol by stirring and ultra sound followed by slowly addition of the fibre-forming hydrophilic polymer while slowly stirring. The resulting suspension was stirred overnight to complete the dissolution of the fibre-forming hydrophilic polymer.

Example 2

Preparation of Alcoholic Gel Ready for Electrospinning—Polyethylene Oxide as Bioadhesive Substance

| Fibre-forming hydrophilic polymer | Bioadhesive substance | | | Solvent Ethanol |
|---|---|---|---|---|
| | Polyethylene oxide - 400.000 | Polyethylene oxide - 2.000.000 | Polyethylene oxide - 4.000.000 | |
| Polyvidone - Kollidon 90F010% | X | x | x | X | x |
| Klucel LF 5% | X | | X | | x |
| Eudragit E 15% | X | | X | | X |
| Eudragit RS 15% | X | x | X | X | X |
| Dermacryl 79 10% | X | | x | | x |

The content of the different dextrans varied between 2.5, 5.0 and 7.5% by weight of the gel or between 25 to 75% by weight of the fibre-forming hydrophilic polymer in those cases where PVP or Dermacryl was used. Experiments have shown that it is possible to use at least up 20% w/w of dextran. The weight ratios between the bioadhesive substance and the hydrophilic polymer are 0.1 to 1.5, namely 0.1, 0.16, 0.25, 0.33, 0.5, 0.75, 1, 1.5.

To prepare the gels Polyethylene oxide was suspended in ethanol by stirring and ultra sound followed by slowly addition of the fibre-forming hydrophilic polymer while slowly stirring. The resulting suspension was stirred overnight to complete the dissolution of the fibre-forming hydrophilic polymer.

Example 3

Preparation of Alcoholic Gel Containing the Drug Substance Imiquimod and Ready for Electrospinning Two different methods were used:

1.5 g of imiquimod was suspended by stirring in 20 g ethanol to which 80 g of a 10% PVP 90K in ethanol was added and stirred slowly for 2 hours.

2.5 g imiquimod was suspended by stirring in 20 g 0.1M acetate buffer pH 4.0 for 2 hours, whereby imiquimod partly dissolves. Then 80 g of a 10% PVP 90.000 in ethanol was added and stirred slowly for 2 hours.

After dissolution of the fibre-forming hydrophilic polymer, imiquimod and the bioadhesive substance were added to obtain a suspension. The suspension was then electrospun as described herein.

The following bioadhesive substances have been used in both methods:
Dextran 500,000 Da
Dextran 750,000 Da
Dextran 2,000,000 Da
Polyethylene oxide 400,000 Da
Polyethylene oxide 2,000,000 Da
Polyethylene oxide 4,000,000 Da The bioadhesive substances were added in proportion to the fibre-forming hydrophilic polymer so that the weight ratio between the bioadhesive substance and the fibre-forming hydrophilic polymer was in the range of from 0.1-5. Specific weight ratios obtained were: 0.2, 0.25, 0.3, 0.4, 0.6, 0.7, 0.75, 0.8, 1, 1.2, 1.25, 1.3, 1.5, 1.6, 1.7, 2, 2.4, 2.7, 3, and 4.

Example 4

Preparation of Fibres Containing the Drug Substance Imiquimod

Two different methods were used:

1.5 g of imiquimod was suspended by stirring in 20 g ethanol to which 80 g of a fibre-forming hydrophilic polymer in ethanol was added and stirred slowly for 2 hours.

2.5 g imiquimod was suspended by stirring in 20 g 0.1M acetate buffer pH 4.0 for 2 hours, whereby imiquimod partly dissolves. Then 80 g of a fibre-forming hydrophilic polymer in ethanol was added and stirred slowly for 2 hours.

The following fibre-forming hydrophilic polymers were used in both methods:
Eudragit® E as a 15% solution in ethanol
Eudragit® RS as a 15% solution in ethanol
Dermacryl 79 as a 10% solution in ethanol The following bioadhesive substances have been used in both methods:
Dextran 500,000 Da
Dextran 750,000 Da
Dextran 2,000,000 Da
Polyethylene oxide 400,000 Da
Polyethylene oxide 2,000,000 Da
Polyethylene oxide 4,000,000 Da The bioadhesive substances were added in proportion to the fibre-forming hydrophilic polymer so that the weight ratio between the bioadhesive substance and the fibre-forming hydrophilic polymer was in the range of from 0.1-2. Specific weight ratios obtained were: 0.2, 0.25, 0.3, 0.4, 0.6, 0.7, 0.75, 0.8, 1, 1.2, 1.25, 1.3, 1.5, 1.6, 1.7, and 2.

After dissolution of the fibre-forming hydrophilic polymer, imiquimod and the bioadhesive substance were added to obtain a suspension. The suspension was then electrospun as described herein.

Example 5

Preparation of Two-Layered Composition Comprising Fibres Containing Imiquimod Layered on a Hydrophobic Backing Layer The fibres described in Example 3 and 4 were prepared, but spun on a hydrophobic layer of containing poly(caprolactone) to obtain a two-layered composition.

Example 6

Preparation of Alcoholic Gel Containing the Drug Substance Betamethasone Di-Proprionate or Clobetasol Propionate and Dextran as Bioadhesive Substance and Ready for Electrospinning

| Ingredients (mg) | Composition | | | |
| --- | --- | --- | --- | --- |
| | I | II | III | IV |
| Polyvidone - Kollidon 90F | 100 | 100 | 100 | 100 |
| Dextran 750.000 | 75 | 75 | 75 | 75 |
| Tributyl citrate | 0 | 50 | 100 | 0 |
| Medium chain glyceride | 0 | 0 | 0 | 75 |
| Betamethasone dipropionate (BDP) or clobetasol propionate | 5 | 5 | 5 | 5 |
| Ethanol | 1000 | 1000 | 1000 | 1000 |

BDP or clobetasol propionate, tributyl citrate and/or medium chain triglyceride were dissolved in ethanol. Then dextran with a molecular weight of approximately 750.000 was added by stirring and ultra sound, and finally Polyvidone 90.000 was added during slowly stirring.

The resulting suspension was stirred overnight to complete the dissolution of the fibre-forming hydrophilic polymer. The suspension was then electrospun as described herein.

Example 7

Preparation of Alcoholic Gel Containing the Drug Substance Betamethasone Di-Proprionate or Clobetasol Propionate and Polyethylene Oxide as Bioadhesive Substance and Ready for Electrospinning

| Ingredients (mg) | Composition | | | | |
| --- | --- | --- | --- | --- | --- |
| | I | II | III | IV | V |
| Eudragit RS | 150 | 150 | 150 | 150 | 150 |
| Polyoxyethylene | 75 | 75 | 75 | 75 | 75 |

-continued

| Ingredients (mg) | Composition | | | | |
|---|---|---|---|---|---|
| | I | II | III | IV | V |
| 750,000 | | | | | |
| Tributyl citrate | 0 | 50 | 100 | 0 | 75 |
| Medium chain glyceride | 0 | 0 | 0 | 75 | 75 |
| Betamethasone dipropionate (BDP) or clobetasol propionate | 5 | 5 | 5 | 5 | 5 |
| Ethanol | 1000 | 1000 | 1000 | 1000 | 1000 |

To prepare an alcoholic gel ready for spinning BDP or clobetasol propionate, Tributyl citrate and/or Medium chain glyceride were dissolved in ethanol. Then polyethylene oxide with a molecular weight of approximately 750.000 was added by stirring and ultra sound, and finally Eudragit RS was added during slowly stirring.

The resulting suspension gel was stirred overnight to complete the dissolution of the fibre-forming hydrophilic polymer. The suspension was electrospun as described herein.

Example 8

Preparation of Alcoholic Gel Containing the Drug Substance Imiquimod and Dextran as Bioadhesive Substance and Ready for Electrospinning

| Ingredients mg | Composition | | | | | |
|---|---|---|---|---|---|---|
| | I | II | III | Iv | V | VI |
| Imiquimod | 25 | 25 | 25 | 25 | 25 | 25 |
| Acetate buffer 0.22M pH 4.65 | 200 | 200 | 200 | 200 | 200 | 200 |
| Acetic acid, glacial | A few drop to dissolve imiquimod | A few drop to dissolve imiquimod | A few drop to dissolve imiquimod | A few drop to dissolve imiquimod | A few drop to dissolve imiquimod | A few drop to dissolve imiquimod |
| Denature Ethanol | 1000 | 1000 | 1000 | 1000 | 1000 | 1000 |
| Luvitec 90K (Polyvinylpyrrolidone (PVP)) | 100 | 100 | 100 | 100 | 0 | 0 |
| Eudragit RS 100 | 0 | 0 | 0 | 0 | 450 | 450 |
| Dextran T750 | 75 | 75 | 75 | 75 | 75 | 75 |
| Tributyl citrate ≥97% | 0 | 50 | 100 | 50 | 0 | 150 |
| Captex 300 (Medium chain glyceride) | 0 | 0 | 0 | 50 | 0 | 0 |

Imiquimod is suspended in acetate buffer to obtain a suspension, wherein imiquimod is partly dissolved. Tributyl citrate and/or medium chain triglyceride were dissolved in ethanol. The imiquimod suspension obtained is added. Then dextran with a molecular weight of approximately 750.000 was added by stirring and ultra sound, and finally Eudragit RS was added during slowly stirring.

The resulting suspension was stirred overnight to complete the dissolution of the fibre-forming hydrophilic polymer. The suspension was then electrospun.

The gels given in the above example were fabricated to sheets using an electrospun manufacturing process with the following settings:

Distance from tip to collector: 25 cm
Electric field at tip: −20 kV
Electric field at collector: −+6 kV
Tip geometry: 18 gauge
Flow rate: 10 ml/h
Temperature: room temperature
Humidity: 60%

Example 9

Preparation of a Two-Layered Composition Containing a Drug-Containing Layer and a Backing Layer

| Ingredients mg | Formulation | | |
|---|---|---|---|
| | I - electrospin | II - coating | III - coating |
| Polyvidone - Kollisone 90F | 100 | 100 | 100 |
| Dextran 750.000 | 75 | 75 | 75 |
| BDP or clobetasol propionate | 5 | 5 | 5 |
| Ethanol | 1,000 | 1,000 | 1,000 |
| Lubrizol - Carbothane | 0 | + | + |

Four compositions were made two of which were without any coating and the II-coating was sprayed on the electrospun fibres, whereas the III coating was made spun on top of the electrospun fibres.

Example 10

In Vivo Adhesion Testing of Compositions

The electrospun fibres exemplified in the examples herein were tested for bioadhesion by placing 1 cm×1 cm sheet on the middle of the tongue. The subject tested the fibres was asked to evaluate the bioadhesiveness on a scale from 0 to 5, where 5 is strong bioadherence and 0 is no bioadherence.

Example 11

Electron Microscopic Analysis

Electron microscope pictures from the two different compositions given in Example 3 are shown in FIG. 1. From the figure it is seen that the size of the drug particles are much smaller in the fibres, where the drug substance is suspended in acetate buffer, i.e. confirming that part of the drug substance is dissolved in the acetate buffer before spinning.

Example 12

In Vitro Adhesion Testing of Electrospun Fibres

Figure 2:
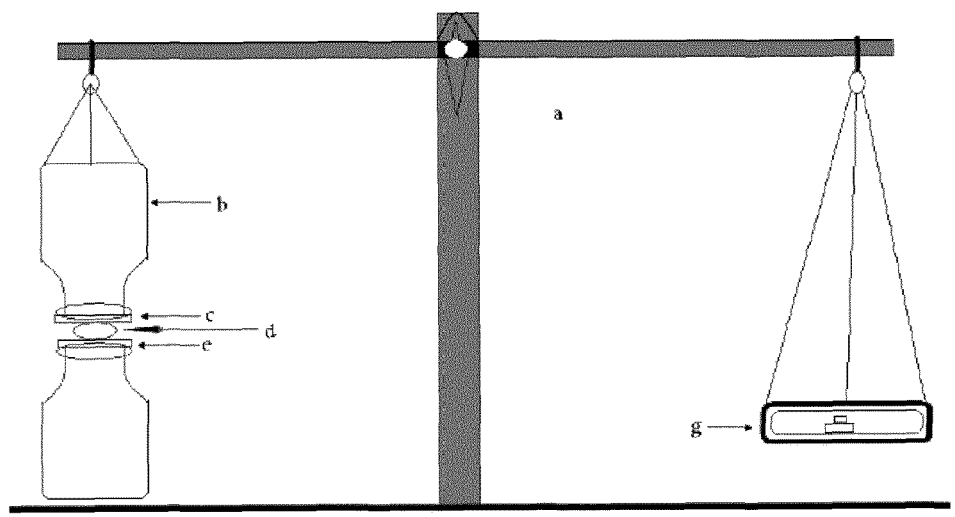
FIG. 2 shows a test apparatus suitable for bioadhesiveness testing.

The bioadhesive forces of the electrospun fibres were determined by means of a bioadhesive measuring device shown in FIG. 2. Buccal mucosa was cut into strips/pieces and washed with tyroide solution. At time of testing a section of buccal mucosa (c) was secured keeping the mucosal side out, on the upper glass vial (B) using rubber band and aluminium cap. The diameter of each exposed mucosal membrane was 1 cm. The vial with the sheep buccal mucosa (C) was stored at 37° C. for 10 min. Then one vial with section of buccal mucosa (C) and another vial were fixed on height adjustable pan (E). To a lower vial electrospun fibres (D) were placed with the help of bilayered adhesive tape, adhesive side facing downward. The height of the lower vial was adjusted so that the electrospun fibres could adhere to the sheep buccal mucosa on the upper vial. A constant force was applied on the upper vial for 2 min, after which it was removed and the upper vial was then connected to the balance. Then the weight on right side pan was slowly added in an increment of 0.5 g till the two vials just separated from each other. The total weight (g) required to detach two vials was taken as a measure of bioadhesive strength. From this bioadhesive strength, the force of adhesive was calculated.

Other suitable methods may also be used such as the in vitro and in vivo methods described by Kockish et al. in Journal of Controlled Release, 77 (2001) 1-6, which is incorporated by reference in its entirety.

Example 13

In Vitro Relase Testing of Compositions

The purpose of the study is to explore the effect of polymer and bioadhesive polymer, plasticizer and oily release-enhancing agent on the in vitro release of betamethasone dipropionate, BDP, or clobetasol propionate from compositions described herein Membrane:

Dow Corning® 7-4107 Silicone Elastomer Membrane, 751 μm.

Diffusion Cell System:

Modified Dialysis Cells.

Receptor compartment: 3.75 ml. The actual volume of each cell is registered by weighing of the assembled cell before and after filling of the receptor compartment. Diameter: 1.55 cm, corresponding to an available diffusion area of 1.89 $cm^2$.

Sheets of silicone membrane are cut to size (circles, 0=22 mm). The membrane is placed between the two compartments of the dialysis cells with the glossy side facing the donor compartment.

The electron spun patch formulation is applied directly onto the membrane by pressing the actuator.

The receptor compartment is filled with preheated and degassed receptor medium (the actual volume of each cell is registered by weighing) and possible air bubbles removed. The sampling arm is sealed with a plastic bung and parafilm to prevent evaporation of the receptor medium. Uniform mixing of the receptor phase is obtained with a magnetic bar placed in the receptor compartment. The diffusion cells are placed in a heating cabinet set at 37° C. to maintain a temperature of 32° C. at the membrane surface. The stirring bed is set.

Receptor Medium:

10% w/w methyl-13-cyclodextrin in 0.05M acetate buffer pH 4.0. The receptor medium is degassed in an ultrasound water bath for minimum 20 minutes prior to the start of the experiment and before 24 h and 48 h sampling. It was ensured that sink conditions were present at all times during the study period; i.e. that the concentration of the drug compounds in the recipient phase was below 10% of the solubility of the drug substances in the medium.

Exposure and Sampling Times:

Samples of 1500 μl (the actual volume is weighed and registered) are withdrawn from each cell at regular time intervals. After each sampling the receptor compartment is re-filled (the exact same volume as withdrawn) with preheated fresh receptor medium. The withdrawn samples are stored in brown sealed HPLC vials at 2-8° C. and protected from light until quantification by HPLC analysis at the end of the experiment. Sampling time points: 0, 1, 6, 24, 30, 48, 54, 72 h.

Study Design:

Each formulation is tested in 3 replicates (n=3).

Example 14

In Vitro Skin Penetration Studies

To investigate the skin penetration and permeation of imiquimod from compositions according to example 3 and 6 a skin diffusion experiment was conducted. Full thickness skin from pig ears was used in the study. The skin was cleaned and kept frozen at −18° C. before use. On the day prior to the experiment the skin was placed in a refrigerator (5±3° C.) for slow defrosting.

Static Franz-type diffusion cells with an available diffusion area of 3.14 $cm^2$ and receptor volumes ranging from 8.6 to 11.1 ml were used in substantially the manner described by T. J. Franz, "The finite dose technique as a valid in vitro model for the study of percutaneous absorption in man", in Current Problems in Dermatology, 1978, J. W. H. Mall (Ed.), Karger, Basel, pp. 58-68. The specific volume was measured and registered for each cell. A magnetic bar was placed in the receptor compartment of each cell. After mounting the skin, physiological saline (35° C.) was filled into each receptor chamber for hydration of the skin. The cells were placed in a thermally controlled water bath which was placed on a magnetic stirrer set at 300 rpm. The circulating water in the water baths was kept at 35±1° C. resulting in a temperature of about 32° C. on the skin surface. After 30 min the saline was replaced by the receptor medium, consisting of 1 part acetate buffer (100 mM, pH 4.0) and 1 part saline.

The in vitro skin permeation of each test composition containing imiquimod was tested in 3 replicates (i.e. n=6). Each test composition was applied on the skin membrane at 0 hours using a pipette. The skin penetration experiment was allowed to proceed for 24 hours. Samples were then collected from the receptor compartments for up to 72 hours.

The concentration of imiquimod in the samples was determined by HPLC.

Example 15

In Vitro Penetration in Buccal Tissue Culture

Figure 3:
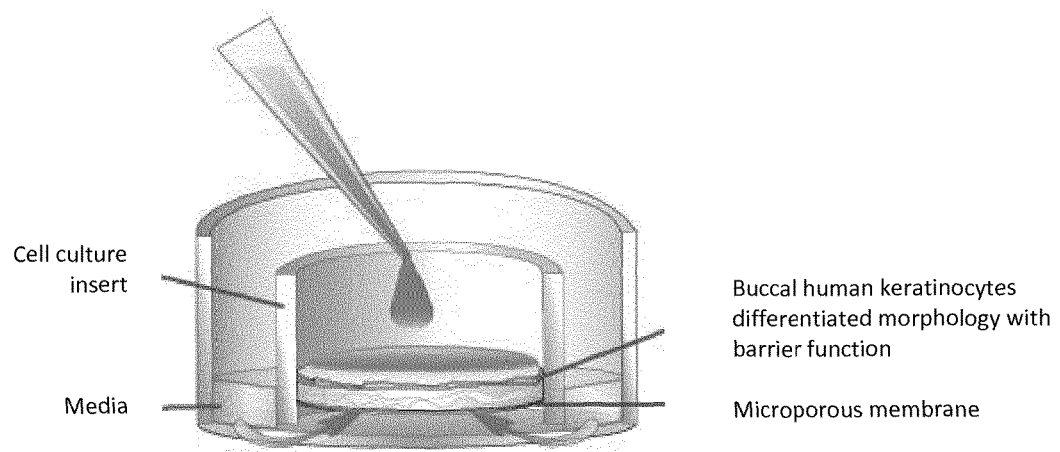
FIG. 3 shows an apparatus for testing buccal penetration.
Figure 4:
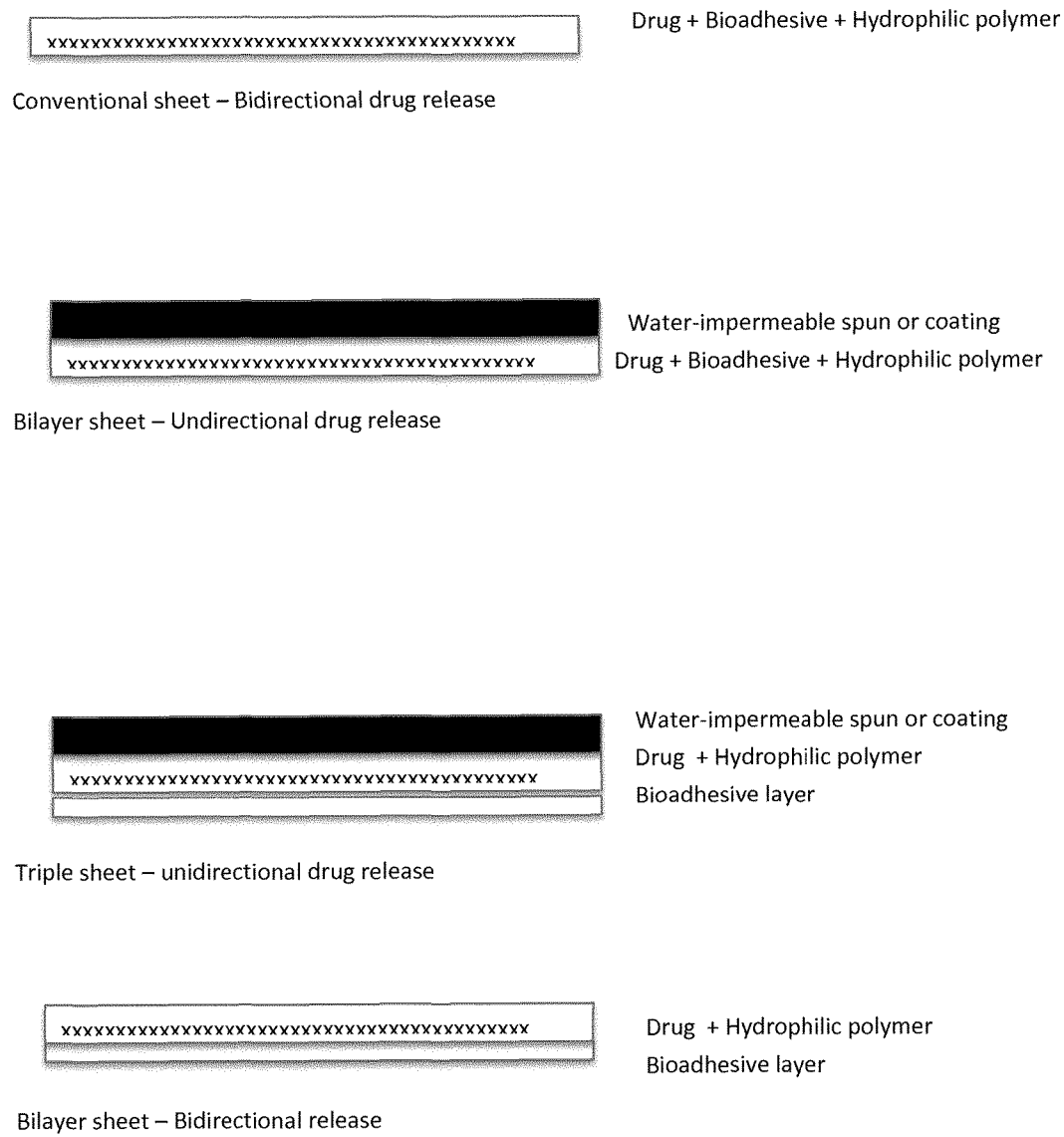
FIG. 4 shows various embodiments of fibres or compositions of the invention.
Figure 5:
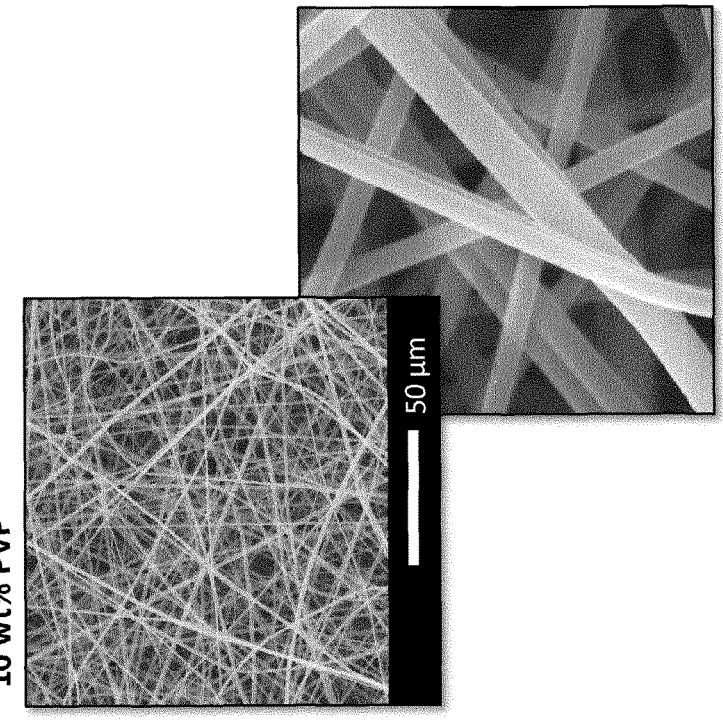
FIG. 5 shows electron microscopy micrographs of a sample of electrospun polyvinylpyrrolidone (PVP). A 10 wt % PVP (Kollidon 90F) solution was prepared by dissolving the appropriate amount of PVP in ethanol and stirring for a minimum time of 3 hours. A volume of the solution (2 mL) was then loaded into a syringe and placed on a syringe pump, pushing the solution through a metallic needle (20 gauge) while a 14 kV electrical current was applied to the needle. This resulted in the formation of a jet of fibres travelling from the tip of the needle to a collecting plate located at a distance of 17 cm. The syringe pump was set at a flow rate of 10 mL/hour. The images show that the material was composed of a mesh of fibres deposited on a random fashion. The fibres generally exhibited a smooth surface and no apparent defects, were cylindrical in shape, and had a diameter under 2 μm.
Figure 6:
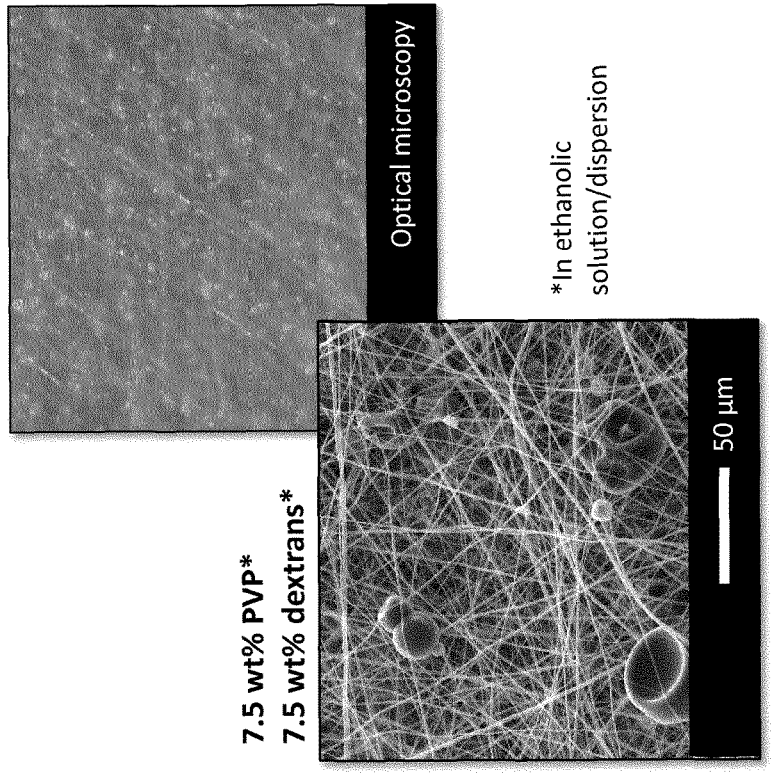
FIG. 6 shows a scanning electron microscopy micrograph of a sample of electrospun PVP with dextran particles located on the surface of the fibres. Electrospinning solutions were prepared by first mixing the appropriate amount of PVP and dextran powders, and then adding ethanol to complete the desired mass. A suspension of dextran particles in dissolved PVP was formed after stirring for a minimum time of 3 hours, which was then used for electrospinning under the conditions described in FIG. 5. Two molecular weights (i.e. 500,000 and 2,000,000) and various amounts of dextrans (i.e. up to 15 wt %) were used in the solutions. The material was composed of random fibres exhibiting a smooth surface and no apparent defects. The dextran particles were generally significantly larger than the fibres and appeared to attach to their surface, although it is possible that smaller particles were also embedded within the PVP fibres. Additionally, the optical microscopy image of an electrospun PVP sample containing dextrans shows that the dextran particles were present on the surface of the material.
Figure 7:
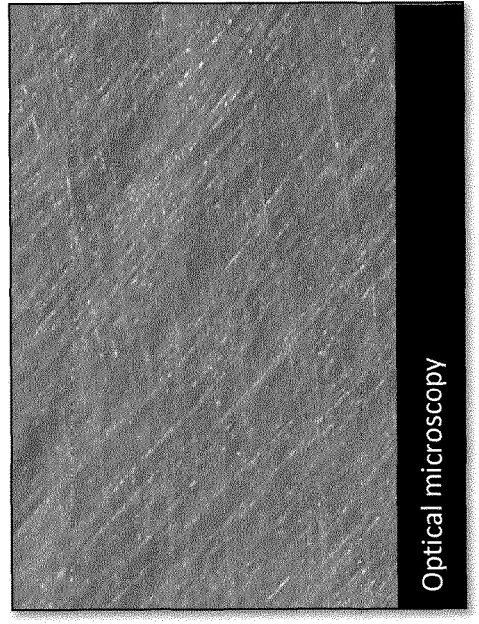
FIG. 7 shows an optical microscopy image of a sample of electrospun PVP containing alcian blue dye. A 10 wt % solution of PVP was prepared by dissolving the appropriate amount of PVP in a 1% w/v solution of alcian blue 8GX in ethanol. The mixture was stirred for a minimum time of 3 hours, and then was electrospun under the conditions described in FIG. 5. It was observed that the surface of the material exhibited a homogeneous blue coloration, demonstrating the potential of electrospun PVP to encapsulate ethanol-soluble substances (i.e. dyes, drugs) within the fibres and to deliver them after dissolution of PVP.
Figure 8:
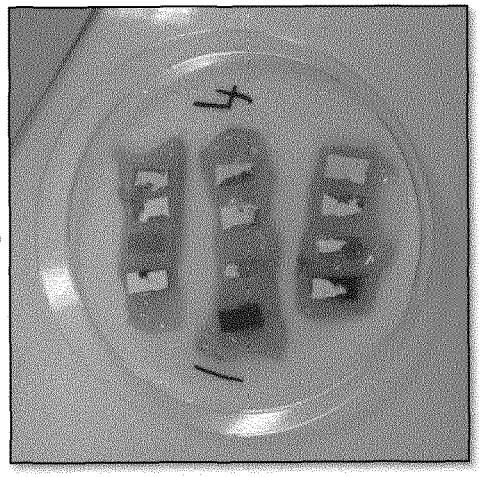
FIG. 8 (left image) illustrates the quick dissolution of a sample of electrospun PVP in artificial saliva. The measured dissolution time was less than 1 second for a sample of dimensions 2 cm×0.5 cm, and was observed to be similar in the case of samples dissolved in other water-based media. This quick dissolution allows for the rapid release of any drug encapsulated within the electrospun fibres. After dissolution, electrospun PVP formed a gel with bioadhesive properties, as observed in FIG. 8 (right image). In this case, several samples of a dual layer system made of electrospun PVP and electrospun poly(caprolactone) (PCL) were placed on pig cheek mucosa sprayed with artificial saliva. The PVP layer quickly formed a gel after contact with the mucosa, while the PCL layer remained undamaged as the material is not water-soluble. Additionally, the PCL layer was able to remain on place for a length of time due to the bioadhesiveness of the PVP gel.
Figure 8:
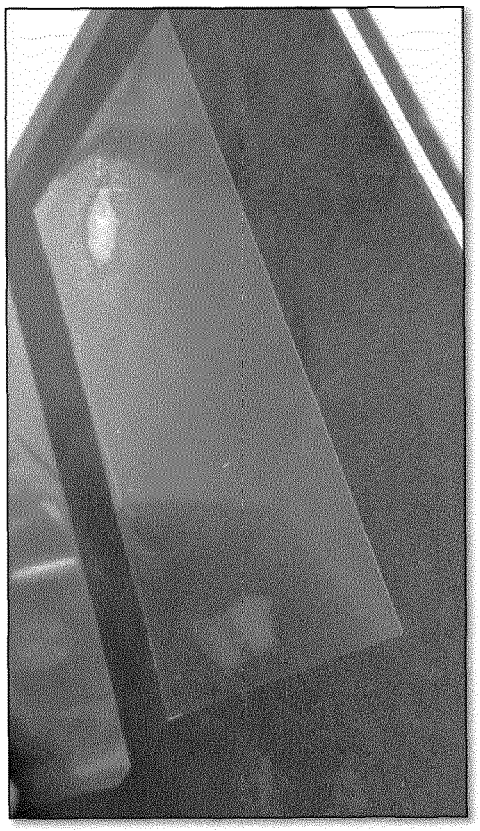
Figure 9:
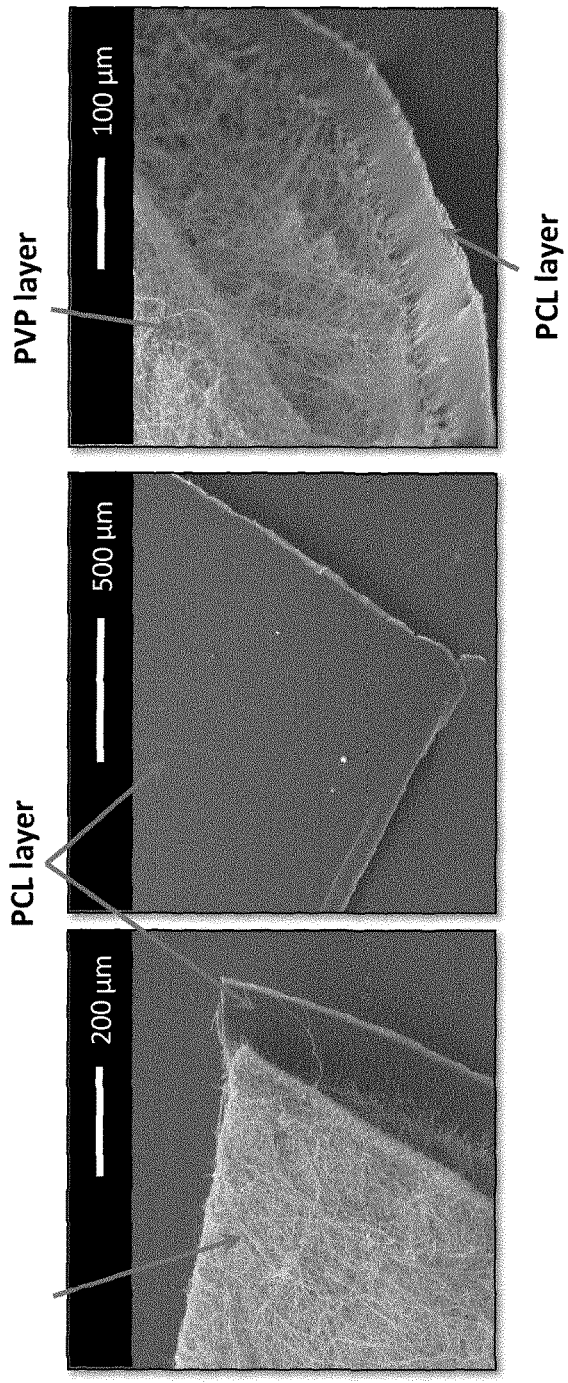
FIG. 9 shows scanning electron microscopy micrographs of a dual layer system made of electrospun PVP and electrospun PCL. These samples were processed using a thermal treatment intended to create an attachment between the two layers. A 10 wt % solution of PVP in ethanol was prepared and electrospun as previously described. Also, a 10 wt % solution of PCL (80,000 average Mw) in a blend of dichloro-methane and dimethylformamide (i.e. DCM/DMF, 90%/10% vol %) was prepared and electrospun on top of the PVP layer. Afterwards, samples were cut from the mats, placed between glass slides, and exposed to a temperature of 65° C. for 15 minutes in an electric furnace. Finally, all the samples were allowed to cool down at room temperature. The images show that the thermal treatment resulted in the melting of the electrospun PCL layer and the subsequent formation of a non-porous and dense film attached to the PVP layer. The PVP layer was unaffected by the thermal treatment due to the melting temperature of PVP being much higher than the melting temperature of PCL (PCL, 60° C., PVP, >180° C.).
Figure 10:
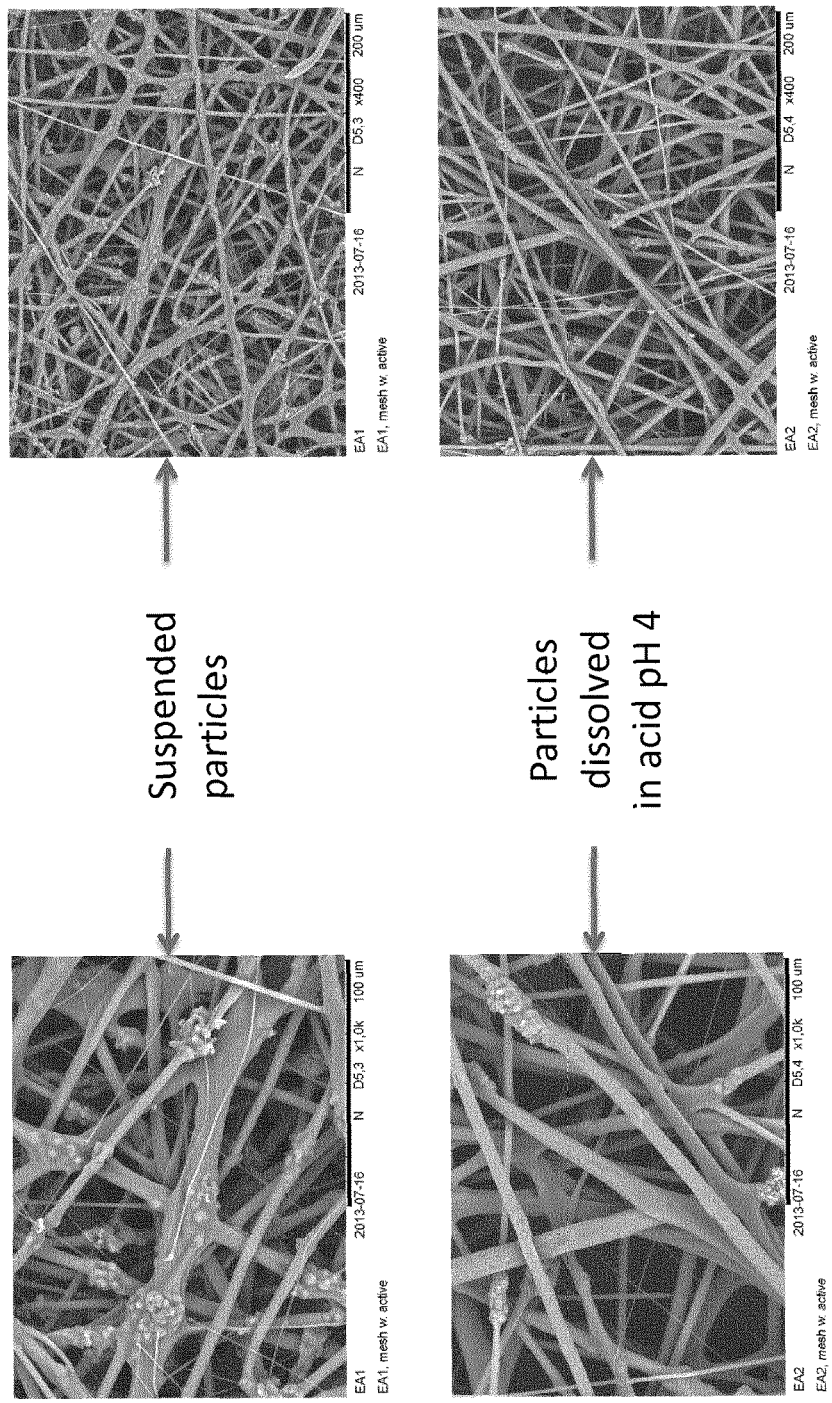
FIG. 10 shows pictures of a sample of electro spun fibres after electro-spinning of a PVP gel with suspended imiquimod.
Figure 11:
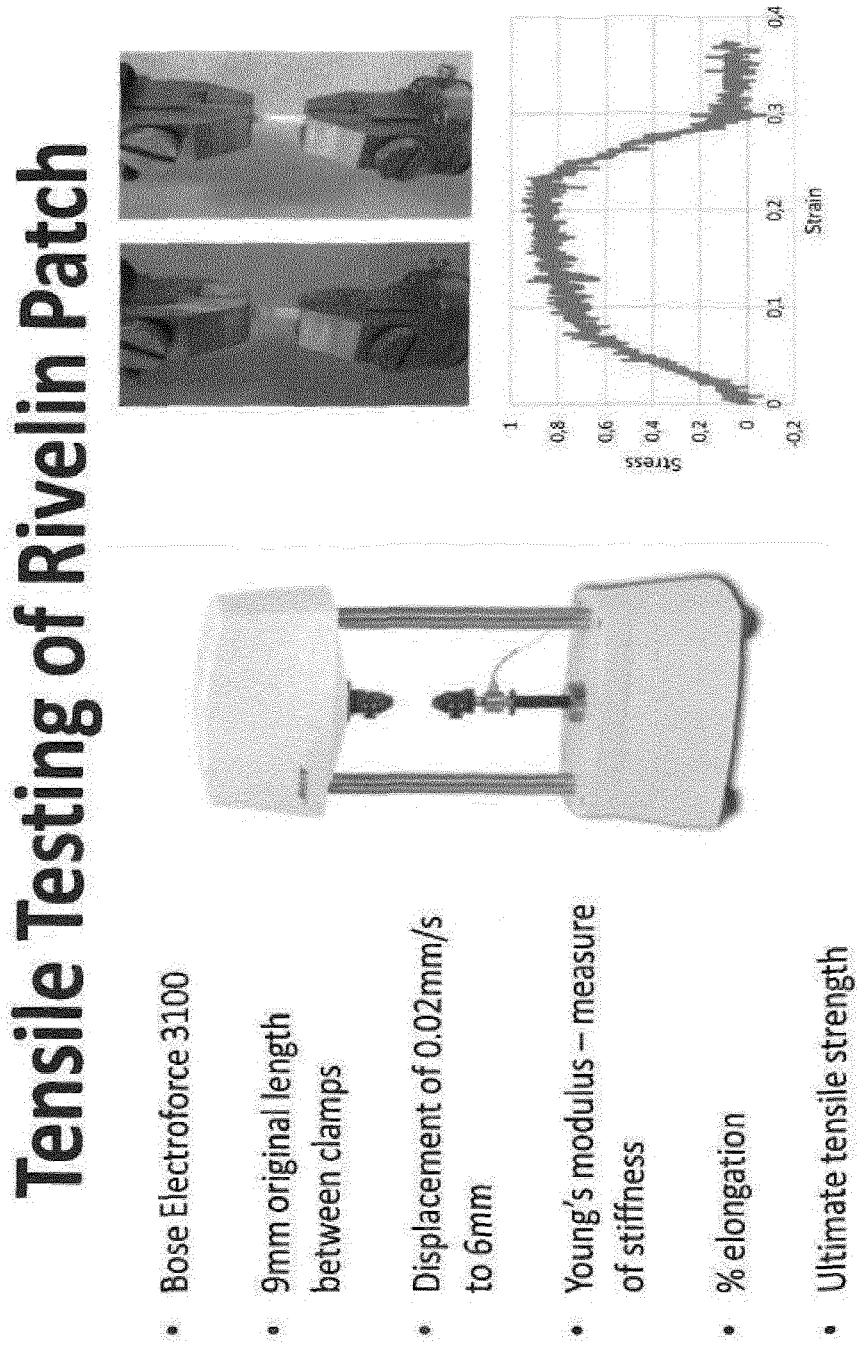
FIG. 11 shows data from tensile testing experiments. Patches are clamped into the claws of a Bose electrophorus 3100 and the arms separated at 0.02 mm/sec. The stress and strain are measured electronically as the patch distends (see graph). From the graph the tensile strength, 5 elongation and Young's modulus (a measure of stress & stain) of the patch is measured.
Figure 12:
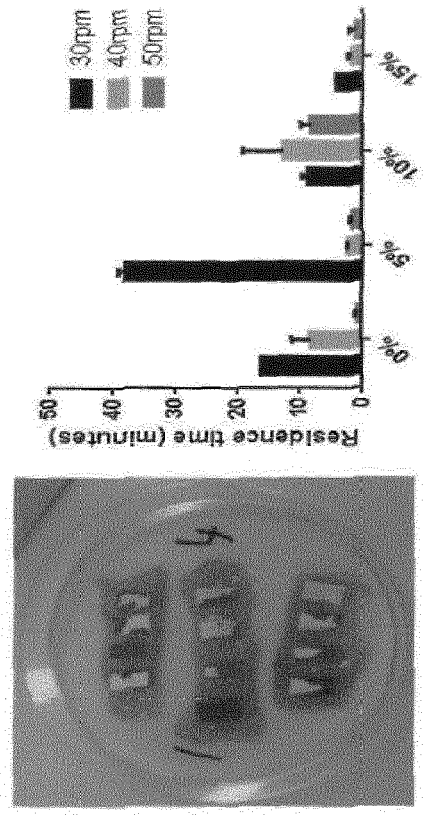
FIG. 12 shows results of an experiment where buccal mucosa isolated from pig cheeks is firmly adhered to a petri dish using cyanoacrelaye glue, and mucosal patches (PVP with increasing % dextran) of equal dimensions are then applied for 5 seconds with approximately equal force and then submerged in PBS and then rotated at different speeds using a mechanical stirrer. The time for the patch to be dislodged from the mucosa is measured in minutes and reported in the right panel.
Figure 13:
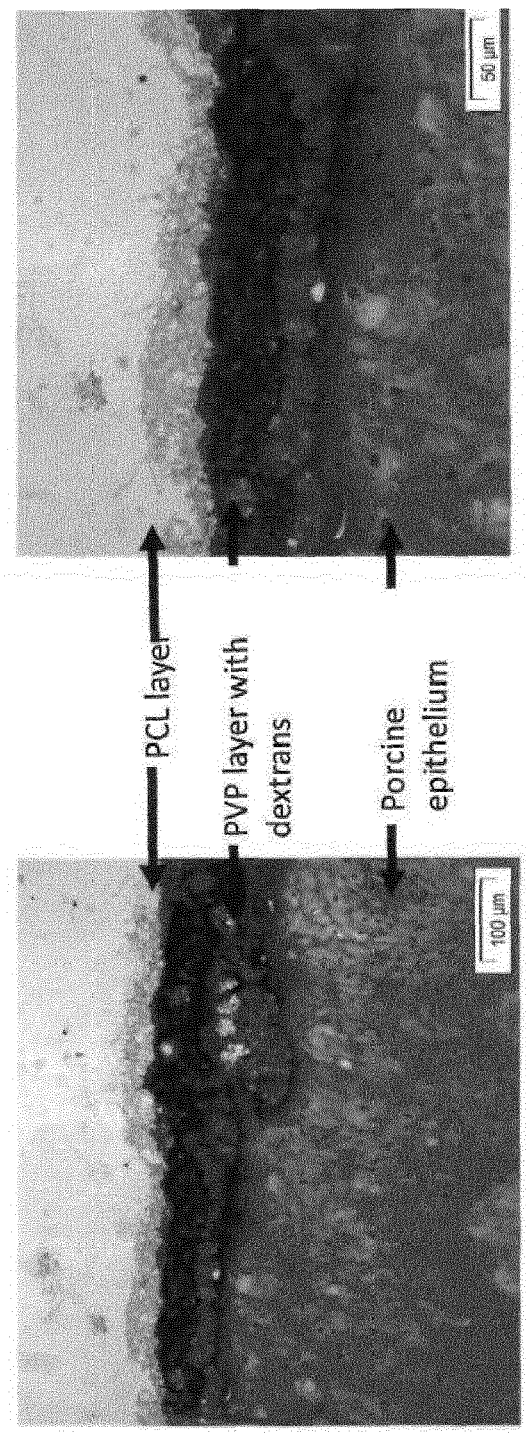
FIG. 13 shows results of an experiment where PCL/PVP (+dextrans) is applied to the surface of pig mucosa with constant force for 30 min, and then the mucosa with patch is snap frozen in liquid nitrogen and then stored at −80 C in optimum cutting temperature mountant, and 8 uM sections were then cut using a cryostat and the sections stained with haemotoxylin and eosin before being mounted on slides. The figure clearly shows that the patch is tightly adhered to but does not penetrate into the mucosal epithelium.
Figure 14:
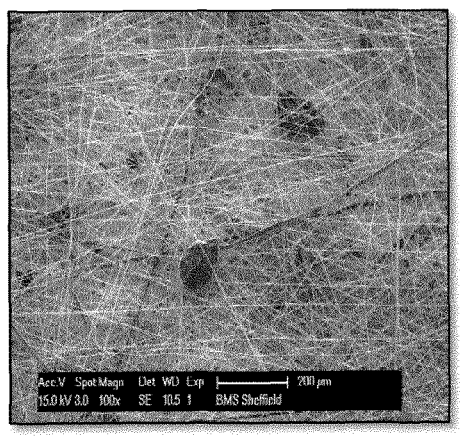
FIG. 14 shows electrospun fibres where Eudragit L100-55 is the fibre-forming hydrophilic polymer. In panels A and B, sodium alginate is a bioadhesive substance, that is present in undissolved form and attached to the fibres. In panels C and D, sodium carboxymethylcellulose has been used as the bioadhesive material.
Figure 14:
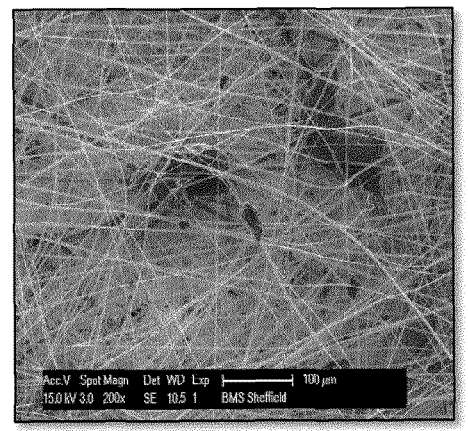
Figure 14:
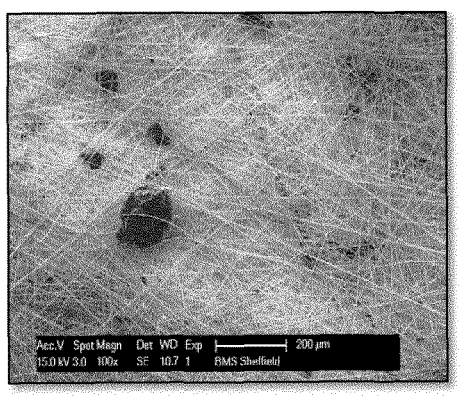
Figure 14:
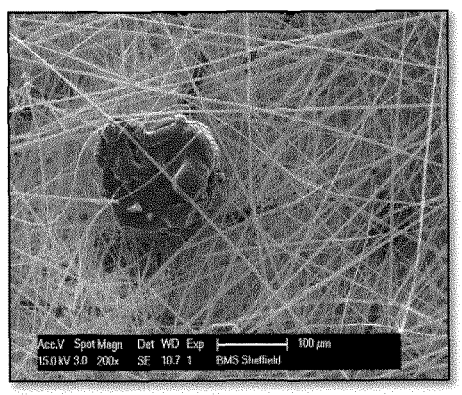
Figure 15:
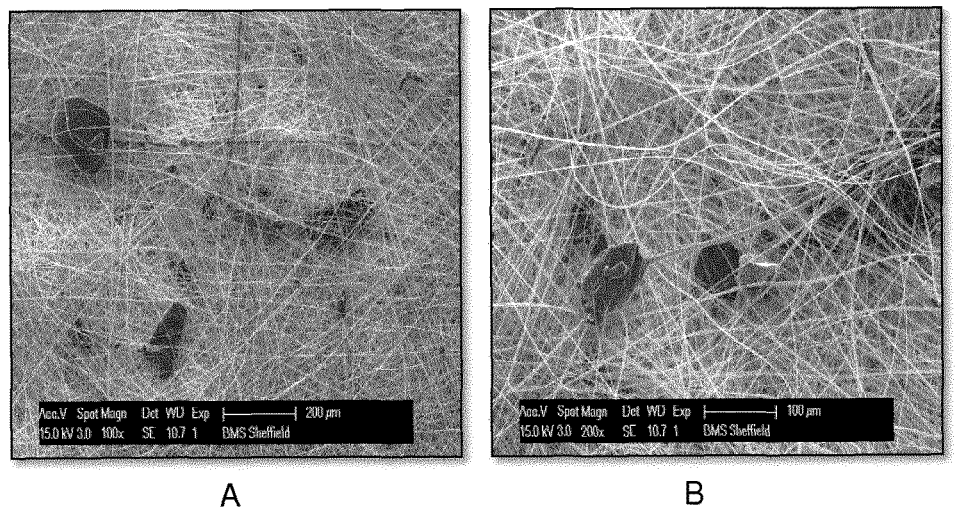
FIG. 15 shows fibres formed with Eudragit 100-55. In panels A and B chitosan was used as a bioadhesive substance. In panels C and D polyvinylalcohol was used as a bioadhesive substance. The bioadhesive material is present in undissolved form attached to the fibres.
Figure 15:
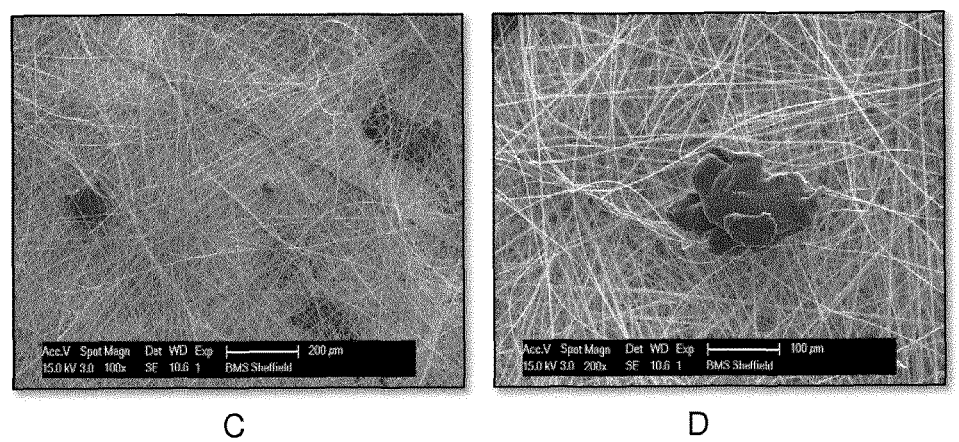
Figure 16:
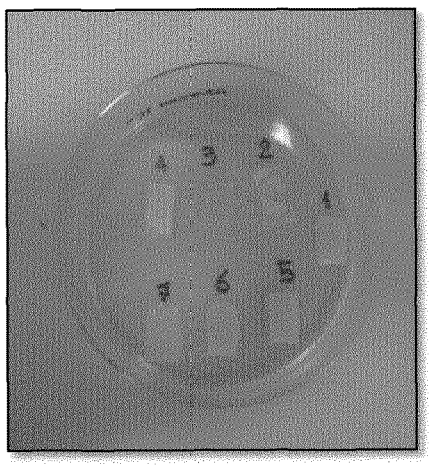
FIG. 16 shows results of bioadhesive tests as described in Example 23.

The apparatus used is shown in FIG. 3.

A bethamethasone dipropionate or clobetasol propionate containing spun sheet formulation is applied directly onto the membrane by pressing the actuator. The cells were kept at 37 C in a heating cabinet. The receptor compartment is filled with preheated receptor medium. The actual volume of each cell is registered by weighing. The receptor medium consists of 10 w/w methyl-13 cyclodekstrin in 0.05M acetate buffer pH 4.0. At different time intervals for up to 48 hours samples of receiver fluid is removed and replaced by fresh preheated receptor medium. Withdrawn samples are stored in brown sealed HPLC vials at 2-8° donor medium and protected from light until quantification by HPLC analysis at the end of the experiment. Each experiment was run in triplicate.

Example 16

In Vitro Skin Irritation Studies in Human Cell Culture

In vitro skin irritation studies in human cell culture was tested in accordance to OECD's Test Guidelines "OECD Guidelines for the testing of chemicals—In Vitro Skin Irritation: Reconstructed Human Epidermis Test Method. 439, adopted 26 Jul. 2013.

Example 17

Determination of Solubility of Bioadhesive Substances

The solubility of the bioadhesive substances was determined using a method recommended by the European Pharmacopoeia 5.0 (Section 5.11, p. 565).

The European Pharmacopoeia uses the following terms to define the solubility of a substance in a particular solvent (Section 1.4, p. 7):

| Descriptive term | Approximate volume of solvent in mL per g of solute |
| --- | --- |
| Very soluble | Less than 1 |
| Freely soluble | From 1 To 10 |
| Soluble | From 10 To 20 |
| Sparingly soluble | From 30 To 100 |
| Slightly soluble | From 100 To 1000 |
| Very slightly soluble | From 1000 To 10000 |
| Practically insoluble | More than 10000 |

The experimental method used to determine the solubility of dextrans and polyethylene oxide is described in the following:

Dissolving Procedure:

Shake tube (1 min) and place in a constant temperature device at a temperature of 25±0.5° C. for 15 min. If the substance is not completely dissolved, repeat the shaking (1 min) and place the tube in the constant temperature device for 15 min.

Method:
1) Weigh 100 mg of finely powdered substance in a stoppered tube (16 mm in internal diameter and 160 mm long), add 0.1 ml of the solvent and proceed as described under Dissolving Procedure. If the substance is completely dissolved, it is very soluble.
2) If the substance is not completely dissolved, add 0.9 ml of the solvent and proceed as described under Dissolving Procedure. If the substance is completely dissolved, it is freely soluble.
3) If the substance is not completely dissolved, add 2.0 ml of the solvent and proceed as described under Dissolving Procedure. If the substance is completely dissolved, it is soluble.
4) If the substance is not completely dissolved, add 7.0 ml of the solvent and proceed as described under Dissolving Procedure. If the substance is completely dissolved, it is sparingly soluble.
5) If the substance is not completely dissolved, weigh 10 mg of finely powdered substance in a stoppered tube, add 10.0 ml of the solvent and proceed as described under Dissolving Procedure. If the substance is completely dissolved, it is slightly soluble.
6) If the substance is not completely dissolved, weigh 1 mg of finely powdered substance in a stoppered tube, add 10.0 ml of the solvent and proceed as described under Dissolving Procedure. If the substance is completely dissolved, it is very slightly soluble.

Materials

Substances:
1) DEX20: Dextran with Mw 2,000,000 (Pharmacosmos)
2) PEO20: Polyethylene oxide with Mw 2,000,000 (Sigma Aldrich)

Solvent:
1) 3 vol % distilled water in ethanol

Results

| Step | DEX20 | PEO20 |
| --- | --- | --- |
| 1 | Not dissolved | Not dissolved |
| 2 | Not dissolved | Not dissolved |
| 3 | Not dissolved | Not dissolved |
| 4 | Not dissolved | Not dissolved |
| 5 | Not dissolved | Not dissolved |
| 6 | Not dissolved | Not dissolved |

Discussion and Conclusions

Both bioadhesive substances (i.e. dextran and polyethylene oxide) had not completely dissolved after the last step of the method recommended by the European Pharmacopoeia, in which 1 mg of substance is added to 10 ml of the solvent.

This means that more than 10,000 ml of solvent are needed to dissolve 1 g of both substances.

Therefore, using the terminology defined in the European Pharmacopoeia, the bioadhesive substances used in the fabrication of a composition of the invention (i.e. dextran and polyethylene oxide) may be described as practically insoluble in 3 vol % distilled water in ethanol.

Example 18

Determination of Maximum Amount of Water Added to Ethanol that Results in the Successful Formation of Fibres The maximum amount of water that can be added to the solvent system was determined by preparing a series of solutions of polyvinylpyrrolidone (PVP) and/or Eudragit RS100 in blends of distilled water and ethanol, which were then electrospun to confirm the formation of fibres.

Composition of Solutions

PVP=10 wt %

Eudragit RS100=0 wt % and 5 wt %

Solvent=blend of distilled water and ethanol at various proportions

Electrospinning Conditions
  15 gauge needle
  Voltage=16 kV
  Distance=19 cm
  Flow rate=5 ml/h
Results

| | | Distilled water (vol %) | | | | | | | | | |
|---|---|---|---|---|---|---|---|---|---|---|---|
| | | 3 | 5 | 10 | 15 | 20 | 30 | 40 | 50 | 60 | 75 | 100 |
| RS100 (wt %) | 0 | ✓ | ✓ | ✓ | ✓ | ✓ | ✓ | ✓ | ✓ | ✓ | ✓ | ✓ |
| | 5 | ✓ | ✓ | ✓ | ✓ | ✓ | ✓ | ✓ | ✓ | ✓ | x | x |

Solutions prepared with up to 50 vol % water were easily processed, generating fibres and materials of good quality.

Solutions prepared with 60 vol % water could generate fibres after modification of the electrospinning conditions. Resulting materials were of unsatisfactory quality.

Solutions made of only PVP with 75 vol % and 100 vol % distilled water could generate fibres after modification of electrospinning conditions. Resulting materials were of unsatisfactory quality.

Solution made of PVP and Eudragit RS100 with 75 vol % and 100 vol % distilled water could not be processed as Eudragit RS100 did not dissolve.

Results

Electrospun PVP and Eudragit RS100 also appear to show increased solubility and reduced material integrity when exposed to water as the water content in the solvent system increases.

Conclusions

Up to 50 vol % distilled water can be added to ethanol and produce good electrospun fibres made of PVP and/or Eudragit RS100.

In practice, the concentration of water in the solvent system used is a balance between i) ensuring a good solubility of the fibre-forming hydrophilic polymer and a poor solubility of the bioadhesive substance, and ii) the properties of the bioadhesive substance upon contact with water; the bioadhesive substance should only to a minor extent affect the viscosity of the solvent system as a highly viscous solvent system makes it difficult to electrospin the fibres.

Increased water content (>20 vol %) in solvent system affects behaviour of PVP+Eudragit RS100 electrospun fibres when exposed to water.

Example 19

Demonstration that Electrospun Fibres May Also be Produced with Additional Polymers Various hydrophilic polymers could be suitable for fibre formation: polyvinylpyrrolidone, polyvinyl alcohol, ethyl cellulose, carboxymethyl cellulose, hydroxypropyl cellulose, acrylates and acrylic copolymers.

A brief literature review of the field was performed in order to learn the potential solution and processing conditions that may facilitate the production of electrospun fibres.

Then, the possibility of electrospinning polymers other than PVP and Eudragit was investigated using solutions of the following polymers in various solvent systems:

1) Poly(vinyl alcohol), 99+% hydrolyzed, Mw 146,000-186,000
2) Sodium carboxymethyl cellulose, Mw~250,000
3) Hydroxypropyl cellulose, Mw~100,000
4) Ethyl cellulose, ethoxyl content 48%, 10 cps Initially, the solvents selected were ethanol and distilled water. According to FAO (Food and Agriculture Organization of the United Nations), the solubility of these polymers in ethanol and water is as follows:

| Polymers | Solubility in ethanol | Solubility in water |
|---|---|---|
| Poly(vinyl alcohol) | Sparingly soluble | Soluble |
| Ethyl cellulose | Soluble if ethyl cellulose contains 46-48% or more of ethoxyl groups | Practically insoluble |
| Hydroxypropyl cellulose | Forms smooth and clear solution at <38° C. | Forms smooth and clear solution at <38° C. |
| Carboxymethyl cellulose | Not soluble | Yields viscous colloidal solution |

Thus, based on this information PVA and CMC are not freely soluble in ethanol.

Poly(Vinyl Alcohol) (PVA)

PVA dissolved in distilled water at (70-90) ° C. under continuous stirring until formation of clear solution.

Concentration=6 wt %

Electrospun fibres formed when using 20 kV and 1.25 ml/h.

Irregular formation of fibres—Currently not adequate for use as a fibre-forming hydrophilic polymer in the fabrication of a composition according to the invention.

Ethyl Cellulose (EC)

EC dissolved well in ethanol and tetrahydrofuran.

Concentration=10-15 wt %

Not possible to electrospin under a wide range of processing conditions, but proper adjustment of process parameters may enable processing of fibres However, could produce electrospun fibres and whole mats by blending with PVP (i.e. 10 wt % PVP and 5 wt % EC)

Resulting material exhibited reduced solubility in water, similar to electrospun PVP and RS100.

Hydroxypropyl Cellulose (HPC)

HPC dissolved well in ethanol and tetrahydrofuran.

Concentration=10-15 wt %

Not possible to electrospin under a wide range of processing conditions, but proper adjustment of process parameters may enable processing of fibres However, could produce electrospun fibres and whole mats by blending with PVP (i.e. 10 wt % PVP and 5 wt % HPC)

Addition of HPC to PVP did not reduce solubility of electrospun fibres.

Carboxymethyl Cellulose (CMC)

CMC dissolved well in distilled water.

Concentration=1-3 wt %

Not possible to electrospin under a wide range of processing conditions.

Results partially improved after blending with polyethylene oxide (CMC:PEO 1:2) and addition of 25 vol % ethanol to distilled water, although fibre formation was not observed.

Conclusions

PVA can be electrospun although current results are not adequate for fabrication of a composition according to the invention.

EC and HPC can be electrospun if blended with PVP.
CMC cannot be currently electrospun.
Results for EC, HPC and CMC differ with what is reported in the literature.
Probably possible with further adjustments of the process parameters.

Example 20

Demonstration of the Spinnability of Various Eudragit Compositions

Various Eudragit compositions were mentioned in the patent, and it was considered important to find out which compositions can be used successfully to produce electrospun fibres.

The following compositions were identified as interesting to be investigated:

| Eudragit | Chemical Composition |
|---|---|
| E100 | Basic Butylated Methacrylate Copolymer |
| L100 | Methacrylic Acid - Methyl Methacrylate Copolymer (1:1) |
| S100 | Methacrylic Acid - Methyl Methacrylate Copolymer (1:2) |
| L100-55 | Methacrylic Acid - Ethyl Acrylate Copolymer (1:1) Type A |
| RL100 | Ammonio Methacrylate Copolymer, Type A |
| RS100 | Ammonio Methacrylate Copolymer, Type B |
| Plastoid B | Neutral copolymer based on butyl methacrylate and methyl methacrylate |

Eudragit RS100
  Ammonio Methacrylate Copolymer, Type B.
  Dissolved in 3 vol % distilled water in ethanol.
  Possible to electrospin.
  Good fibre formation when blended with PVP.
Eudragit L100-55
  Methacrylic Acid—Ethyl Acrylate Copolymer (1:1) Type A.
  Dissolved in ethanol.
  Possible to electrospin forming materials of good quality.
  If a blend of two or more fibre-forming hydrophilic polymers are used for fibre formation, then the polymers used should be able to blend in the solvent system used and they should be dissolved.

Example 21

Molecular Weight of Bioadhesive Substances Used

The aim of this example is to demonstrate that the bioadhesive substances suggested for use in a composition of the invention can be employed within the molecular weight ranges stated.

One requirement is that the bioadhesive substance must not be freely soluble in the solvent system used, the solubility should be sparingly soluble or less. This sets a limitation with respect to molecular weight as eg dextran and PEO with low molecular weight do not fulfil the solubility criteria.

Our experimental work had demonstrated:
  Bioadhesive strength of a polymer tends to increase as the molecular weight increases.
  This is related to the critical molecular length necessary to produce an interpenetrating layer and entanglements with the surface of the soft tissues.
  In the case of polyethylene oxide, which has a highly linear configuration, adhesive strengths increases up to molecular weights of 4,000,000.
  In the case of dextrans, which present a more coiled configuration, are reported to display similar bioadhesive strengths at both low and high molecular weights due to 'shielding' of the functional dextran groups.
  For polyethylene oxide, an experimental study of the bioadhesive properties of the electrospun composition was performed using PEO with molecular weights of 400,000 and 2,000,000.
  Although there were no significant differences between both compositions, the patches with polyethylene oxide of 2,000,000 presented results with smaller variability and greater average adhesion times.
  For dextrans, the experimental study was performed on electrospun materials containing dextrans with molecular weights of 500,000 and 2,000,000.
  Similarly, although there were no significant differences between both compositions, the patches with dextrans of 2,000,000 presented results with greater average adhesion times.
  In conclusion, the high molecular weights substances were selected in the bioadhesion study as they exhibited more clearly defined results than those of lower molecular weight.

Example 22

Determination of Maximum Amount of Bioadhesive Substance that can be Added to the Electrospinning Solution The maximum amount of bioadhesive substances that can be added to the electrospun materials was determined by preparing a series of solutions of polyvinylpyrrolidone (PVP) in ethanol with increasing amounts of bioadhesive substance, which were then electrospun to confirm the formation of fibres.

Composition of Solutions
  PVP=10 wt %
  Bioadhesive substances=polyethylene oxide, Mw 2,000,000 (PEO20) and dextrans, Mw 2,000,000 (DEX20)
  Solvent=ethanol
Electrospinning Conditions
  15 gauge needle
  Voltage=16 kV
  Distance=19 cm
  Flow rate=5 ml/h
Results

|  | Content (wt %) | | | | | |
|---|---|---|---|---|---|---|
|  | 5 | 10 | 20 | 30 | 40 | 50 |
| DEX20 | ✓ | ✓ | ✓ | ✓ | ✓ | x |
| PEO20 | ✓ | ✓ | ✓ | ✓ | x | — |

Solutions with up to 30 wt % DEX20 and 20 wt % PEO20 were easily processed, generating fibres and materials of good quality.
Solutions with 40 wt % DEX20 and 30 wt % PEO20 could be electrospun but the resulting materials were of unsatisfactory quality due to the high viscosity of the solution.
Preparations with 50 wt % DEX20 and 40 wt % PEO20 could not be processed. Their viscosity was too high to be electrospun, and their appearance was more paste-like than solution-like.

Example 23

Demonstration that Electrospun Fibres May Also be Produced Using Additional Bioadhesive Substances Experiments with a range of bioadhesive substances other than dextran and polyethylene oxide have been performed.

A brief literature review of the field was performed in order to identify potential bioadhesive substances that may be added to the electrospun fibres. Then, the following hydrophilic substances were proposed:

| Bioadhesive | Solubility in ethanol | Solubility in water |
|---|---|---|
| Sodium alginate | Not soluble | Dissolves slowly, forming a viscous solution |
| Sodium carboxymethyl cellulose | Not soluble | Forms viscous colloidal solution |
| Chitosan | Not soluble | Not soluble unless pH <6 or deacetylated |
| Poly(vinyl alcohol) | Sparingly soluble | Soluble |

The substances used were:
1) Alginic acid sodium salt from brown algae, medium viscosity
2) Sodium carboxymethyl cellulose, Mw~250,000
3) Chitosan, medium molecular weight
4) Poly(vinyl alcohol), 99+% hydrolyzed, Mw 146,000-186,000

Particle size of the substances as supplied was too large to be added to the electrospun fibres. Therefore, all substances were milled and sieved to produce powders with particle size <150 μm.

Electrospinning solutions were then prepared and processed under the following conditions:
20 wt % Eudragit L100-55 in ethanol+10 wt % bioadhesive substance
15 gauge needle
Voltage=16 kV
Distance=19 cm
Flow rate=2.5 ml/h
The results showed that other bioadhesive substances are suitable for use in the present context.
Poly(vinyl alcohol) and chitosan particles were visible after drying of the samples while the other substances were not apparent. This suggests that poly(vinyl alcohol) and chitosan may be the substances with the least bioadhesive potential due to slow dissolution in water at room temperature.

Example 24

Fibre Formation of PVP Using Ethanol as Solvent

Experiments were conducted to investigate whether fibre-formation of PVP is dependent on the concentration of PVP in ethanol. The following results were obtained:
1) 2.5 wt % PVP—No formation of fibre. Electrospraying (i.e. formation of particles rather than fibres) was observed instead, even after reducing the flow rate to 2.5 mL/h and 1 mL/h.
2) 5 wt % PVP—Fibre formation was observed. Good formation of membrane made of individual fibres.
3) 7.5 wt % PVP—Fibre formation was observed. Good formation of membrane made of individual fibres.
4) 10 wt % PVP—Fibre formation was observed. Good formation of membrane made of individual fibres.
5) 12.5 wt % PVP—Fibre formation was observed. Good formation of membrane made of individual fibres.
6) 15 wt % PVP—Fibre formation was observed. Good formation of membrane made of individual fibres.
7) 20 wt % PVP—Fibre formation was observed. Membrane made of individual fibres could be fabricated after reducing flow rate to 2.5 mL/h and increasing the distance to collector to 23 cm.
8) 25 wt % PVP—Fibre formation was observed. A membrane could be fabricated after reducing the flow rate to 1 mL/h and increasing the distance to collector to 23 cm. However, the resulting membrane was of less good quality than the fibres obtained in 1)-7).

All solutions were prepared in ethanol.

The electrospinning conditions were as follows, except when otherwise indicated:
Voltage=15 kV
Flow rate=5 mL/h
Distance to collector=19 cm The diameter of the fibres was observed to increase as the concentration of PVP increased. In the case of 20 wt % and 25 wt % PVP this resulted in slower solvent evaporation and the fusion of the fibres after deposition, forming a film. In these cases the distance to the collector was increased to 23 cm in order to obtain membranes made of individual fibres. Additionally, the area of fibre deposition on the collector decreased as the concentration increased.

The viscosity of 20 wt % and 25 wt % PVP was significantly greater than in the other solutions, probably causing the issues with fibre formation mentioned above. In the specific case of 25 wt % it was difficult to eliminate air bubbles from the solution prior to electrospinning due to its viscous nature. Fibres could be generated from 20 wt % and 25 wt %.

These results suggested that the optimal range of PVP concentrations for the fabrication of fibres according to the invention may be between 5 wt % and 20 wt %, with concentrations around 10 wt % producing very good results.

The invention claimed is:

1. Electrospun fibers comprising
   (i) a hydrophilic polymer that is soluble in a first solvent, wherein the hydrophilic polymer comprises one or more selected from polyvinylpyrrolidone (PVP), ethylcellulose, hydroxypropylcellulose, acrylates, polymers of acrylic/methacrylic esters, and mixtures thereof;
   (ii) a bioadhesive substance that has a solubility in said first solvent of 0.5 g/100 ml or less at 25° C., wherein the bioadhesive substance comprises one or more selected from dextrans, polyethylene oxides (PEOs), alginate, tragacanth, carrageenan, pectin, guar, xanthan, gellan, methylcellulose, hydroxypropylmethylcellulose (HPMC), polyvinylalcohol (PVA), polymers of acrylic acids (PAAs), chitosan, lectins, thiolated polymers, nonionic water-soluble polyethylene oxide resins (polyox WSR), and PAA polyethylene glycol copolymers (PAA-co-PEG), and mixtures thereof; and
   (iii) optionally, a drug substance,
   wherein at least a portion of the bioadhesive substance is attached to the fibers as particles in an undissolved form, wherein the portion of the bioadhesive substance attached to the fibers in an undissolved form is not an integral part of the fibers.

2. Electrospun fibers according to claim 1 comprising the optional drug substance.

3. Electrospun fibers according to claim 1, wherein the hydrophilic polymer has a solubility in said first solvent of 3 g/100 ml or more at 25° C.

4. Electrospun fibers according to claim 1, wherein the bioadhesive substance is at the most very slightly soluble in said first solvent at 25° C.

5. Electrospun fibers according to claim 1, wherein at least 90% w/w of the bioadhesive substance is present in undissolved form.

6. Electrospun fibers according to claim 1, wherein at least 95% w/w of the bioadhesive substance is present in undissolved form.

7. Electrospun fibers according to claim 1, wherein said first solvent is ethanol or an ethanol-water mixture.

8. Electrospun fibers according to claim 7, wherein said first solvent is an ethanol-water mixture containing 10% v/v water or less.

9. Electrospun fibers according to claim 7, wherein said first solvent is an ethanol-water mixture containing 5% v/v water.

10. Electrospun fibers according to claim 1, wherein the hydrophilic polymer comprises PVP, polymers of acrylic/methacrylic esters, or mixtures thereof.

11. Electrospun fibers according to claim 1, wherein the bioadhesive substance comprises dextran having an average molecular weight of from 400,000 Da to 2,000,000 Da.

12. Electrospun fibers according to claim 1, wherein the bioadhesive substance comprises dextran having an average molecular weight of about 2,000,000 Da.

13. Electrospun fibers according to claim 1, wherein the bioadhesive substance comprises polyethylene oxide having an average molecular weight of from 100,000 Da to 4,000,000 Da.

14. Electrospun fibers according to claim 1, wherein the bioadhesive substance comprises polyethylene oxide having an average molecular weight of 2,000,000 Da.

15. Electrospun fibers according to claim 1, wherein the weight ratio between the bioadhesive substance and the hydrophilic polymer in the fibers is in a range of from 0.1 to 10.

16. Electrospun fibers according to claim 1, wherein the drug substance is selected from drug substances indicated for treatment of a disease of the skin or mucosa.

17. Electrospun fibers according to claim 1, wherein the drug substance is selected from drug substances indicated for treatment of a disease in the oral cavity.

18. Electrospun fibers according to claim 17, wherein the drug substance is selected from drug substances indicated for local treatment of a disease in the oral cavity.

19. Electrospun fibers according to claim 1, wherein the water content of the fibers is at the most about 5% w/w.

20. Electrospun fibers according to claim 1, further comprising a coating provided on an outer surface of the electrospun fibers.

21. Electrospun fibers according to claim 20, wherein the coating is water-impermeable.

22. Electrospun fibers according to claim 21, wherein the coating comprises one or more of carbothane, polycaprolactone, and polyethylene-co-vinyl acetate.

23. A composition comprising electrospun fibers according to claim 1.

24. A composition according to claim 23, wherein the concentration of the electrospun fibers in the composition is from 70 to 100% w/w.

25. A composition according to claim 23 in the form of a layered composition.

26. A pharmaceutical composition comprising electrospun fibers according to claim 2.

27. A kit comprising (i) a composition according to claim 23, and (ii) an applicator for applying the composition in an oral cavity.

28. A method for preparing electrospun fibers according to claim 2, comprising:
    (i) dissolving the hydrophilic polymer in the first solvent to obtain a solution;
    (ii) suspending the bioadhesive substance in the solution to obtain a dispersion;
    (iii) adding the drug substance to the dispersion to obtain a mixture; and
    (iv) electrospinning the mixture;
    wherein, in the electrospun fibers, at least 90% w/w of the bioadhesive substance is present as particles in an undissolved form attached to the fibers.

29. A method for preparing electrospun fibers according to claim 2, comprising:
    (i) dissolving the hydrophilic polymer in a first portion of the first solvent to obtain a solution;
    (ii) dissolving or suspending the drug substance in the first solution to obtain a mixture;
    (iii) suspending the bioadhesive substance in a second portion of the first solvent to obtain a dispersion,
    (iv) dual-electrospinning the mixture obtained and the dispersion,
    wherein, in the electrospun fibers, at least 90% w/w of the bioadhesive substance is present as particles in an undissolved form attached to the fibers.

30. Electrospun fibers prepared by electrospinning a composition comprising (i) a hydrophilic polymer, (ii) a bioadhesive substance, (iii) a first solvent and (iv) optionally, a drug substance, wherein
    the hydrophilic polymer is soluble in the first solvent and comprises one or more selected from polyvinylpyrrolidone (PVP), ethylcellulose, hydroxypropylcellulose, acrylates, polymers of acrylic/methacrylic esters, and mixtures thereof;
    the bioadhesive substance has a solubility in the first solvent of 0.5 g/100 ml or less at 25° C. and comprises one or more selected from dextrans, polyethylene oxides (PEOs), alginate, tragacanth, carrageenan, pectin, guar, xanthan, gellan, methylcellulose, hydroxypropylmethylcellulose (HPMC), polyvinylalcohol (PVA), polymers of acrylic acids (PAAs), chitosan, lectins, thiolated polymers, nonionic water-soluble polyethylene oxide resins (polyox WSR), and PAA polyethylene glycol copolymers (PAA-co-PEG), and mixtures thereof,
    wherein at least a portion of the bioadhesive substance is attached to the fibers as particles in an undissolved form, wherein the portion of the bioadhesive substance attached to the fibers in an undissolved form is not an integral part of the fibers.

* * * * *